(12) United States Patent
Michihata

(10) Patent No.: US 10,313,629 B2
(45) Date of Patent: Jun. 4, 2019

(54) MEDICAL OBSERVATION DEVICE

(71) Applicant: Sony Olympus Medical Solutions Inc., Tokyo (JP)

(72) Inventor: Taihei Michihata, Kanagawa (JP)

(73) Assignee: Sony Olympus Medical Solutions Inc., Tokyo (JP)

( * ) Notice: Subject to any disclaimer, the term of this patent is extended or adjusted under 35 U.S.C. 154(b) by 281 days.

(21) Appl. No.: 15/083,516

(22) Filed: Mar. 29, 2016

(65) Prior Publication Data

US 2016/0323539 A1 Nov. 3, 2016

(30) Foreign Application Priority Data

Apr. 30, 2015 (JP) .................................. 2015-093674
Feb. 4, 2016 (JP) .................................. 2016-020283

(51) Int. Cl.

| H04N 7/10 | (2006.01) |
| H04N 17/00 | (2006.01) |
| H04N 7/22 | (2006.01) |
| A61B 1/00 | (2006.01) |
| H04N 7/18 | (2006.01) |

(52) U.S. Cl.
CPC ........... *H04N 7/10* (2013.01); *A61B 1/00009* (2013.01); *H04N 7/22* (2013.01); *H04N 17/004* (2013.01); *H04N 7/183* (2013.01)

(58) Field of Classification Search
CPC ......... H04N 7/10; H04N 17/004; H04N 7/183
USPC ......................................................... 348/43
See application file for complete search history.

(56) References Cited

U.S. PATENT DOCUMENTS

| 2006/0052664 A1* | 3/2006 | Julian | A61B 1/0053 600/146 |
| 2008/0027284 A1* | 1/2008 | Suda | A61B 1/00055 600/134 |
| 2008/0262299 A1* | 10/2008 | Niida | A61B 1/05 600/110 |
| 2009/0058997 A1* | 3/2009 | Kato | H04N 7/183 348/65 |

(Continued)

FOREIGN PATENT DOCUMENTS

JP 2009-61032 3/2009

*Primary Examiner* — Tung T Vo
(74) *Attorney, Agent, or Firm* — Oblon, McClelland, Maier & Neustadt, L.L.P.

(57) ABSTRACT

A medical observation apparatus includes: an image sensor that outputs an image signal; a transmission signal processing unit configured to convert an electrical signal into serial electrical signals and change number and a destination thereof; an optical signal conversion unit configured to convert the serial electrical signals into optical signals; optical transmission paths configured to transmit the converted optical signals; an electrical signal conversion unit configured to convert the transmitted optical signals into serial electrical signals; a received-signal processing unit configured to performs a predetermined image processing on the received serial electrical signals to generate and output a display image signal to a display device, and detect transmission failure of the optical signals in the optical transmission paths; and a control unit configured to control changing of the number and the destination of the serial electrical signals in accordance with a result of detection of the transmission failure.

2 Claims, 14 Drawing Sheets

(56) References Cited

U.S. PATENT DOCUMENTS

| | | | |
|---|---|---|---|
| 2009/0179985 A1* | 7/2009 | Amling | G06F 19/327 348/65 |
| 2012/0320176 A1* | 12/2012 | Tanaka | A61B 1/00006 348/65 |
| 2013/0096380 A1* | 4/2013 | Matsuzawa | A61B 1/00013 600/109 |
| 2013/0169775 A1* | 7/2013 | Ono | A61B 1/00009 348/68 |
| 2014/0340496 A1* | 11/2014 | Okawa | A61B 1/00006 348/65 |
| 2015/0164331 A1* | 6/2015 | Burgess | A61N 7/02 600/410 |
| 2016/0206185 A1* | 7/2016 | Kinouchi | A61B 1/04 |
| 2017/0095137 A1* | 4/2017 | Kinouchi | A61B 1/04 |

\* cited by examiner

MEDICAL OBSERVATION DEVICE

CROSS-REFERENCE TO RELATED APPLICATIONS

This application claims the benefit of Japanese Priority Patent Application JP 2015-93674 filed Apr. 30, 2015, and Japanese Priority Patent Application JP 2016-020283 filed Feb. 4, 2016, the entire contents of which are incorporated herein by reference.

BACKGROUND

The present disclosure relates to a medical observation device.

In the past, in the medical field, an endoscope device is used to observe internal organs of a subject, for example, a patient. For example, the endoscope device includes an endoscope (hereinafter, referred to as a camera head), a control device, and a transmission cable. The endoscope includes an image sensor. The control device controls the operation of the camera head and displays an image of the inside of a subject on a display device by processing the image signal picked up by the image sensor. The transmission cable electrically connects the camera head and the control device and transmits various signals.

In recent years, an image sensor having a large number of pixels enabling an image observation with a higher resolution has been developed, and the application thereof to an endoscope device is being studied. In accordance with this trend, adaptation of an optical transmission system that transmits signals using laser light is also being studied, to transmit a large number of signals between the image sensor and the control device at a high speed (see, for example, Japanese Laid-open Patent Publication No. 2009-61032).

SUMMARY

In general, the transmission cable and the control device are separable and are connected with connectors thereof. Thus, in the endoscope device, an image signal converted into an optical signal in the camera head may not be transmitted to the control device with an optical cable (an optical transmission path). In other words, an optical signal is transmitted from the camera head to the control device, through an optical cable in a transmission cable, an optical connection unit of a connector of the transmission cable, an optical connection unit of a connector of the control device, and an optical cable in the control device. When the connection surfaces of the optical connection units through which the light passes are soiled or fogged, or when there is angle deviation between the optical paths of the optical connection units, the optical signal is attenuated and a transmission failure on the optical signal occurs, resulting in the problem that an image suitable for observation may not be displayed.

The transmission failure on the optical signal also occurs when the cable is deteriorated over time or with use. An electrical cable deteriorating over time or for other reasons tends to break after noise due to the deterioration is gradually superimposed on signals and appears as image noise. Thus, the operator can easily recognize the abnormal state at a relatively early stage. However, in the optical cable, the optical fiber portion breaks suddenly, and leads to image loss. Hence, there is the problem that an image may be lost during the procedure.

There is a need for a medical observation apparatus that can detect transmission failure of optical signals in an optical transmission path and that can continuously transmit image signals to a control device even if the transmission failure occurs in the optical transmission path.

According to one aspect of the preset disclosure, there is provided a medical observation apparatus including: an image sensor that includes a plurality of pixels arranged in a matrix, the pixels performing photoelectric conversion on light from a subject irradiated with irradiation light to generate an image signal and that outputs the image signal; a transmission signal processing unit configured to convert an electrical signal output from the image sensor into a plurality of serial electrical signals and configured to change number and a destination of the serial electrical signals to be output; an optical signal conversion unit configured to convert the serial electrical signals into optical signals; a plurality of optical transmission paths configured to transmit the optical signals converted by the optical signal conversion unit; an electrical signal conversion unit configured to convert the optical signals transmitted by the optical transmission paths into a plurality of serial electrical signals; a received-signal processing unit configured to performs a predetermined image processing on the received serial electrical signals converted by the electrical signal conversion unit to generate a display image signal, output the generated display image signal to a display device, and detect transmission failure of the optical signals in the optical transmission paths; and a control unit configured to control changing of the number and the destination of the serial electrical signals output by the transmission signal processing unit in accordance with a result of detection of the transmission failure performed by the received-signal processing unit.

DETAILED DESCRIPTION

Figure 1:
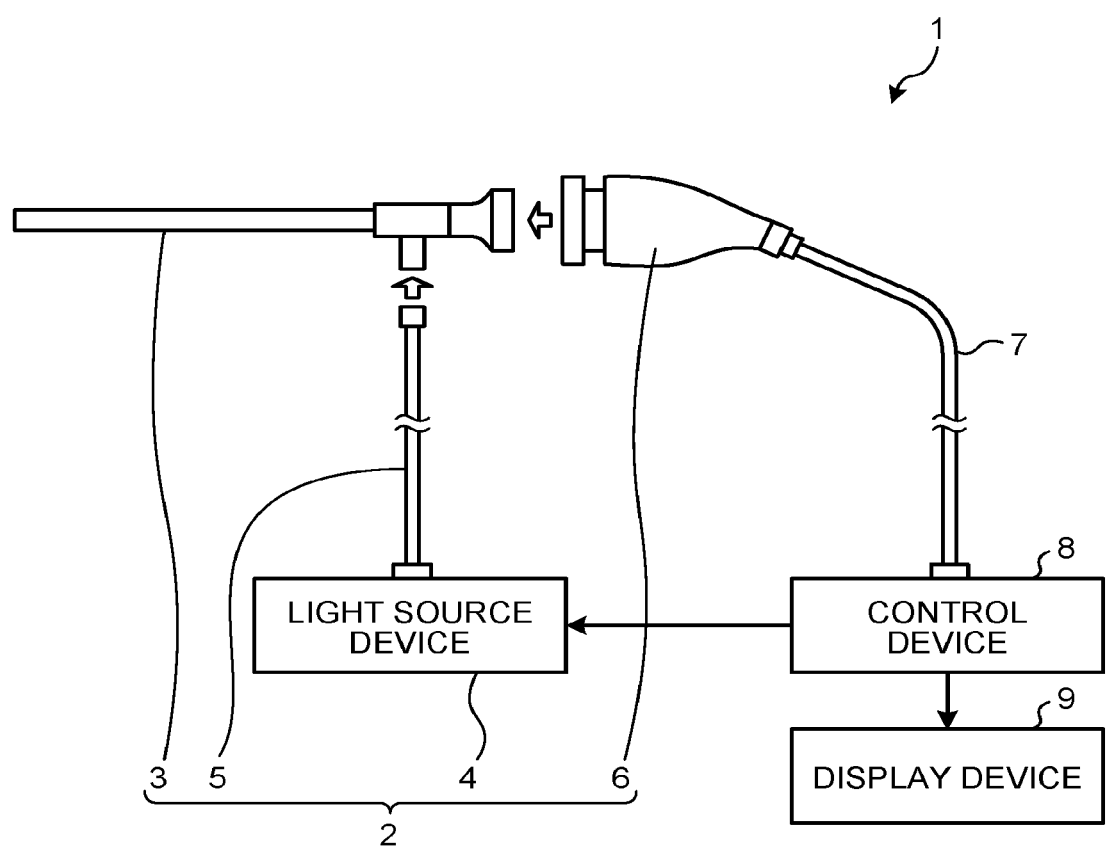
FIG. 1 is a diagram of a schematic configuration of an endoscope device according to a first embodiment of the present disclosure.

The following describes an endoscope device as exemplary aspects to embody the present disclosure (hereinafter, referred to as "embodiments"). The embodiments are not intended to limit the disclosure. Like components are denoted by like reference numerals and symbols in the drawings.

First Embodiment

FIG. 1 is a diagram of a schematic configuration of an endoscope device according to a first embodiment of the present disclosure. An endoscope device 1 is used in the medical field to observe the inside of an observation target, such as a human (inside of a living body). As illustrated in FIG. 1, the endoscope device 1 includes an endoscope 2, a transmission cable 7, a control device 8, and a display device 9. While the present embodiment describes the endoscope device 1 including a rigid borescope (inserting unit 3 (FIG. 1)) in the endoscope 2, it is not limited thereto. The endoscope device 1 may include a flexible borescope (not illustrated) in the endoscope 2. While the first embodiment describes the endoscope device 1 including a camera head 6 (FIG. 1) in the endoscope 2, it is not limited thereto. The endoscope device 1 may be an endoscope device (ultrasound endoscope) including an ultrasound probe as the endoscope 2.

The endoscope 2 examines the inside of a living body (inside of a subject) and outputs the examination result. As illustrated in FIG. 1, the endoscope 2 includes the inserting unit 3, a light source device 4, a light guide 5, and the camera head 6.

The inserting unit 3 is hard, has an elongated shape, and is to be inserted inside the body. The inserting unit 3 includes an optical system that includes one or more lenses and condenses an image of a subject.

The light source device 4 is connected to a first end of the light guide 5 to supply light for irradiating the inside of the living body to the first end of the light guide 5.

The first end of the light guide 5 is detachably connected to the light source device 4, and a second end thereof is detachably connected to the inserting unit 3. The light guide 5 transmits the light supplied from the light source device 4 from the first end to the second end, thereby supplying the light to the inserting unit 3. The light supplied to the inserting unit 3 is output from the distal end of the inserting unit 3 to the inside of the living body. The light output to the inside of the living body (subject image) is collected by the optical system in the inserting unit 3.

The camera head 6 is detachably connected to the proximal end of the inserting unit 3. The camera head 6 captures the subject image collected by the inserting unit 3 under the control of the control device 8 and outputs image signals obtained by the capturing. The camera head 6 performs photoelectric conversion on the image signals, thereby converting them into optical signals and then outputs the optical signals. The configuration of the camera head 6 will be described later in greater detail.

A first end of the transmission cable 7 is detachably connected to the control device 8, and a second end thereof is connected to the camera head 6. Specifically, the transmission cable 7 includes a plurality of electrical wires (not illustrated) and a plurality of optical cables (not illustrated) on the inner side of an outer cover serving as the outermost layer. The electrical wires transmit control signals, synchronization signals, clocks, and electric power output from the control device 8 to the camera head 6. The optical cables transmit image signals (optical signals) output from the camera head 6 to the control device 8. The transmission cable 7 according to the first embodiment transmits the optical signals through an optical cable group 71 including four optical cables 71a to 71d, which will be described later. The transmission cable 7 also transmits the electrical signals through a plurality of electrical wires 72, which will be described later.

The control device 8 includes a central processing unit (CPU) and other components and collectively controls the operations of the camera head 6 and the display device 9. The control device 8 performs predetermined image processing on the image signals obtained by capturing performed by the camera head 6. The configuration of the control device 8 will be described later in greater detail.

Under the control of the control device 8, the display device 9 displays various types of information including the image to which predetermined image processing is performed by the control device 8. Thus, the operator can observe a desired position inside a subject and determine the properties thereof by operating the endoscope 2 while looking at the image (in-vivo image) displayed on the display device 9. The display device 9 includes a liquid crystal display, an organic electroluminescence (EL) display, or the like.

Figure 2:
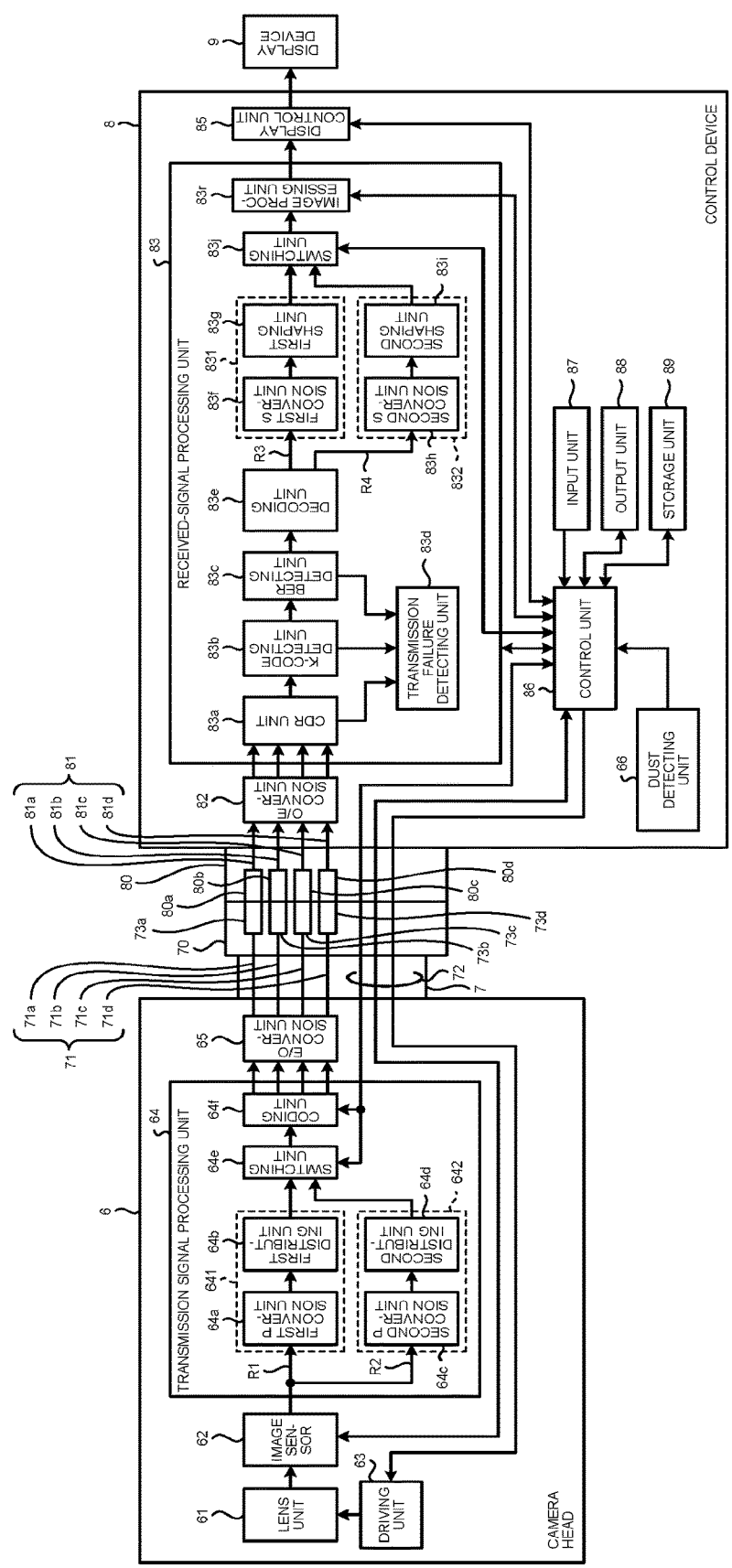
FIG. 2 is a block diagram of a configuration of a camera head in an endoscope, a transmission cable, and a control device illustrated in FIG. 1.

The following describes the configuration of the camera head 6, the transmission cable 7 including the optical cable group 71 of the four optical cables 71a to 71d (optical transmission paths) and the electrical wires 72, and the control device 8. FIG. 2 is a block diagram of the configuration of the camera head 6 in the endoscope 2, the transmission cable 7, and the control device 8.

As illustrated in FIG. 2, the camera head 6 includes a lens unit 61, an image sensor 62, a driving unit 63, a transmission signal processing unit 64 (serial conversion unit), and an electro/optical (E/O) conversion unit 65 (optical signal conversion unit).

The lens unit 61 includes one or more lenses and forms the subject image collected by the inserting unit 3 on an image-capturing surface of the image sensor 62. The one or more lenses can be moved along an optical axis. The lens unit 61 includes an optical zoom mechanism (not illustrated)

that changes the angle of view and a focus mechanism (not illustrated) that changes the focus by moving the one or more lenses.

The image sensor 62 captures the inside of the subject under the control of the control device 8. The image sensor 62 includes a light-receiving unit (not illustrated), a reading unit (not illustrated), an analog front end (AFE) (not illustrated), and a control unit (not illustrated). The light-receiving unit includes a plurality of pixels arranged in a matrix. The pixels receive light from the subject irradiated with light and perform photoelectric conversion on the received light, thereby generating image signals. The reading unit reads the image signals (electrical signals) generated by the pixels. The AFE performs various types of processing, such as noise rejection and analog/digital (A/D) conversion, on the image signals (analog) read by the reading unit. The control unit controls the operation of the image sensor 62 based on the control signals received from the control device 8. The image sensor 62 serially outputs the image signals (digital). The image sensor 62, for example, is a complementary metal-oxide semiconductor (CMOS) image sensor that can perform exposure and reading on each horizontal line. The image sensor 62 may be a charge-coupled device (CCD) image sensor. The image signals generated by the image sensor 62 are serially output to the transmission signal processing unit 64 as live image signals in a RAW format or image signals in a predetermined format with a low compression rate. The image signals (electrical signals) output from the image sensor 62 may be output not serially but in parallel.

The driving unit 63 causes the optical zoom mechanism and the focus mechanism to operate under the control of the control device 8, thereby changing the angle of view and the focus, respectively, in the lens unit 61.

The transmission signal processing unit 64 converts the electrical signals serving as the image signals output from the image sensor 62 into a plurality of serial electrical signals. The transmission signal processing unit 64 includes a first transmitter-side signal conversion unit 641, a second transmitter-side signal conversion unit 642, a switching unit 64e (first switching unit), and a coding unit 64f. The transmission signal processing unit 64, for example, is a programmable integrated circuit, such as a field-programmable gate array (FPGA).

The first transmitter-side signal conversion unit 641 includes a first parallel (P) conversion unit 64a and a first distributing unit 64b. The first transmitter-side signal conversion unit 641 converts the electrical signals output from the image sensor 62 into parallel electrical signals of a first group number equal to the number of the optical cables in the transmission cable 7, which will be described later. In the example illustrated in FIG. 2, the optical cable group 71 in the transmission cable 7 includes the four optical cables 71a to 71d. The first P conversion unit 64a converts the electrical signals output from the image sensor 62 into parallel electrical signals of four groups. The first distributing unit 64b adjusts the parallel electrical signals of four groups converted by the first P conversion unit 64a in predetermined units of bytes and distributes them in a manner corresponding to the respective four optical cables 71a to 71d. The first distributing unit 64b outputs the parallel electrical signals adjusted in a manner enabling delimiters between the signals to be identified so as to distribute the parallel signals of four groups to the respective four optical cables 71a to 71d. The first distributing unit 64b thus distributes the parallel electrical signals of the respective groups in a manner corresponding to the four cables.

The second transmitter-side signal conversion unit 642 includes a second P conversion unit 64c and a second distributing unit 64d. The second transmitter-side signal conversion unit 642 compresses the electrical signals output from the image sensor 62 and converts them into parallel electrical signals of a second group number smaller than the first group number equal to the number of the optical cables. The second transmitter-side signal conversion unit 642 then distributes the parallel electrical signals. In the example illustrated in FIG. 2, the second P conversion unit 64c compresses the electrical signals output from the image sensor 62 to convert them into parallel electrical signals of three groups the number of which is smaller than that of the optical cables 71a to 71d by 1. The second distributing unit 64d adjusts the parallel electrical signals of three groups converted by the second P conversion unit 64c in predetermined units of bytes and distributes them in a manner corresponding to respective predetermined three cables of the four optical cables 71a to 71d. The optical cable (e.g., the optical cable 71a) positioned outermost in the optical cable group 71 is generally susceptible to the effect of bending and other factors in the use of the transmission cable 7. As a result, the optical cable 71a is more likely to be broken than the other transmission cables 71b to 71d, for example. To address this, the second distributing unit 64d distributes the parallel electrical signals of three groups converted by the second P conversion unit 64c in a manner corresponding to the respective three optical cables 71b to 71d. The second distributing unit 64d outputs the parallel electrical signals adjusted in a manner enabling delimiters between the signals to be identified so as to distribute the parallel signals of three groups to the respective three optical cables 71b to 71d. The second distributing unit 64d thus distributes the parallel electrical signals of the respective groups in a manner corresponding to the three cables. To use the same external clock as that of the first transmitter-side signal conversion unit 641, for example, the transmission rate in the second transmitter-side signal conversion unit 642 is set to a compression rate obtained by multiplying the eternal clock using a phase locked loop (PLL) or the like.

The switching unit 64e can switch the parallel electrical signals to be received by the coding unit 64f between the parallel electrical signals of the first group number output from the first distributing unit 64b and the parallel electrical signals of the second group number output from the second distributing unit 64d under the control of a transmission failure detection unit 83d of the control device 8, which will be described later. In other words, the switching unit 64e switches the electrical signals to be received by the E/O conversion unit 65 via the coding unit 64f between the parallel electrical signals of the first group number and the parallel electrical signals of the second group number. The switching unit 64e is a multiplexer, for example.

The coding unit 64f performs N-bit/M-bit coding (N<M, and a bit is hereinafter represented by "b") on the parallel electrical signals of the respective groups received from the switching unit 64e. The coding unit 64f performs 8 b/10 b coding on the received parallel electrical signals based on a stored conversion table, thereby converting 8 b electrical signals into 10 b electrical signals. Alternatively, the coding unit 64f performs 64 b/66 b coding on the received parallel electrical signals based on the stored conversion table, thereby converting 64 b electrical signals into 66 b electrical signals. Alternatively, the coding unit 64f performs 64 b/67 b coding on the received parallel electrical signals, thereby converting 64 b electrical signals into 67 b electrical signals. Alternatively, the coding unit 64f performs 128 b/130 b coding on the received parallel electrical signals, thereby converting 128 b electrical signals into 130 b electrical signals. Subsequently, the coding unit 64f converts the parallel electrical signals of the respective groups into serial electrical signals. The transmission signal processing unit 64 performs various types of processing, such as superimposition of clock signals and insertion of a K-code to the start position and the end position of valid data, on the serial electrical signals resulting from the processing performed by the coding unit 64f. The transmission signal processing unit 64 then outputs the serial electrical signals to the E/O conversion unit 65. The image signals received by the coding unit 64f may be received not as parallel electrical signals but as serial electrical signals. In this case, the first transmitter-side signal conversion unit 641 and the second transmitter-side signal conversion unit 642 output the image signals as serial electrical signals without converting them into parallel electrical signals.

The E/O conversion unit 65 converts the serial electrical signals received from the coding unit 64f into optical signals. The E/O conversion unit 65 then outputs each optical signal converted to any one of the optical cables 71a to 71d corresponding thereto. If the E/O conversion unit 65 receives four serial electrical signals from the coding unit 64f, the E/O conversion unit 65 outputs the four optical signals converted to the respective four optical cables 71a to 71d. If the E/O conversion unit 65 receives three serial electrical signals from the coding unit 64f, the E/O conversion unit 65 outputs the three optical signals converted to the respective three optical cables, that is, to the respective optical cables 71b to 71d, for example.

A dust detecting unit 66 detects accumulation of dust in the control device 8, which will be described later, and outputs the detection result to a control unit 86 of the control device 8 through the electrical wires 72. If the accumulation amount of dust detected by the dust detecting unit 66 exceeds a predetermined threshold, the control unit 86 causes the display device 9 or an output unit 88, which will be described later, to output alarm information. The alarm information indicates that fan lock may have been occurring or indicates a potential risk of abnormal temperature rise in the apparatus because of a short in a circuit or reduction in the airflow volume caused by the accumulation of dust.

Figure 3:
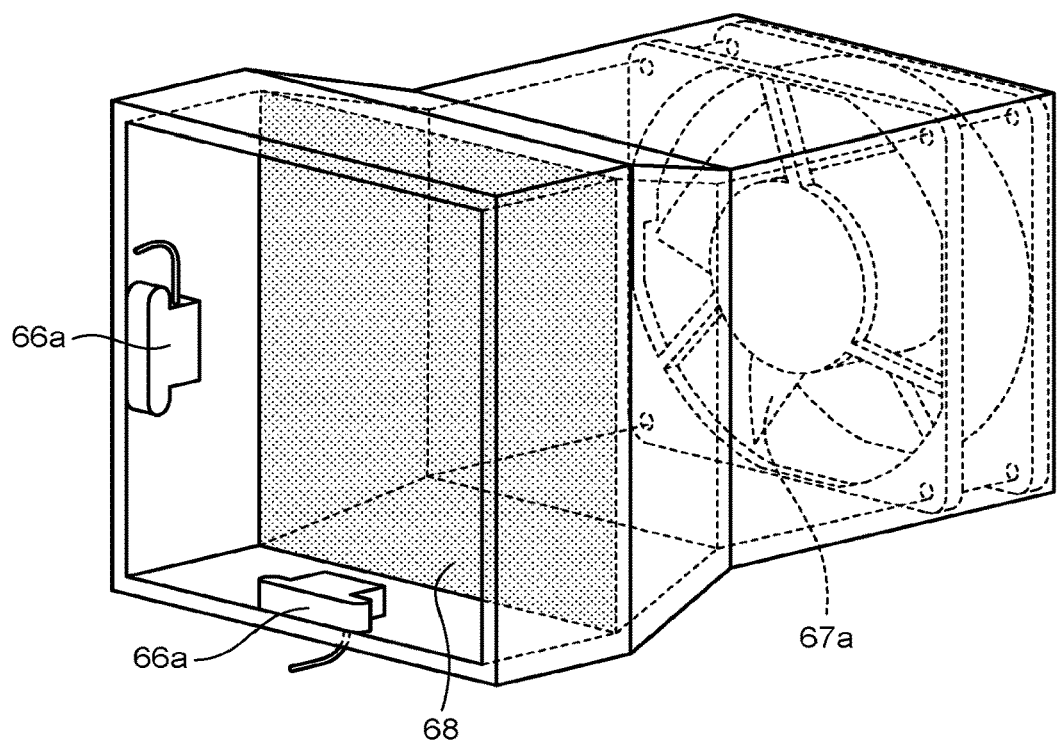
FIG. 3 is a perspective view of a part of the inside of the control device illustrated in FIG. 2.
Figure 4:
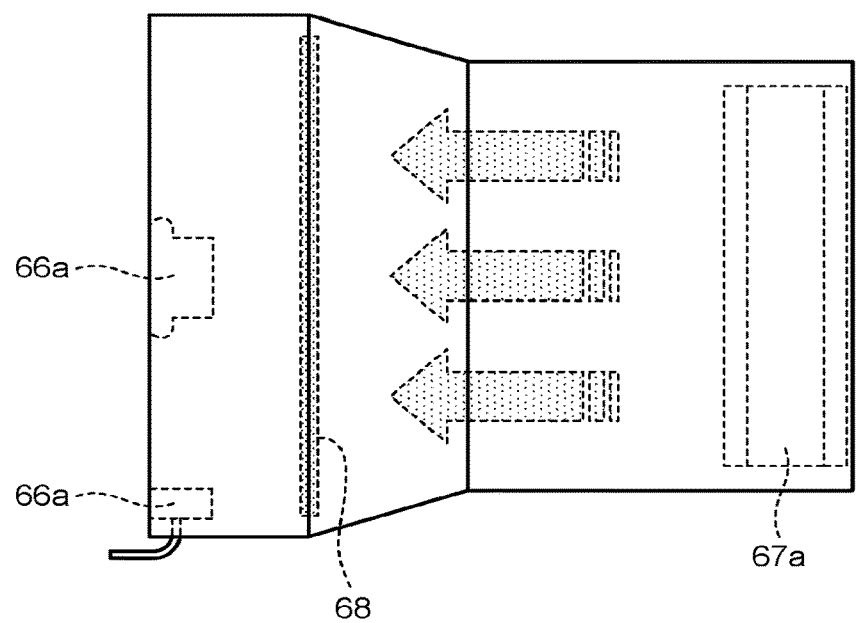
FIG. 4 is a right side view of the control device illustrated in FIG. 3.

FIG. 3 is a perspective view of a part of the inside of the control device 8. As illustrated in FIG. 3, the dust detecting unit 66 is a flow sensor 66a, for example, and is provided on the outer side of a filter 68 arranged on the air-outlet side of a fan 67a of the control device 8. FIG. 4 is a right side view of the control device 8 illustrated in FIG. 3. As illustrated in FIG. 4, airflow coming out from the fan 67a as indicated by the arrow is discharged through the filter 68. The flow sensor 66a detects the volume of airflow coming out of the filter 68. Accumulation of dust on the filter 68 decreases the volume of airflow. If the volume of airflow detected by the flow sensor 66a falls below a predetermined threshold, the control unit 86 performs output processing of the alarm information. The dust detecting unit 66 may be an optical sensor that optically detects dust. In this case, the dust detecting unit 66 is provided to a portion on which dust is likely to accumulate. If the amount of detected dust exceeds a predetermined threshold, the control unit 86 performs output processing of the alarm information. The dust detecting unit 66 may be a dedicated circuit for dust detection. If the circuit is shorted out by dust, the control unit 86 performs output processing of the alarm information. The dust detecting unit 66 is provided near at least one of the fan and the filter and may be provided to a corner and other portions of the case on which dust is likely to accumulate. While a plurality of flow sensors 66a are provided in the example illustrated in FIGS. 3 and 4, the number thereof may be one.

The transmission cable 7 includes a connector 70 (transmitter-side connector), the optical cable group 71 including the four optical cables 71a to 71d (first optical transmission paths), and the electrical wires 72. The connector 70 is detachably connected to a connector 80 of the control device 8, which will be described later. The transmission cable 7 and the camera head 6 serve as an image-capturing device.

The distal ends of the optical cables 71a to 71d are connected to the E/O conversion unit 65, and the proximal ends thereof are provided with respective optical connection units 73a to 73d (transmitter-side optical connection units). The optical connection units 73a to 73d are provided to the connector 70. The optical connection units 73a to 73d each include a GRIN lens connected to an optical fiber end surface of the optical cables 71a to 71d, respectively, and a cover glass that covers the surface of the GRIN lens.

The control device 8 includes the connector 80 (receiver-side connector), an optical cable group 81 including a plurality of optical cables 81a to 81d (second optical transmission paths), an O/E conversion unit 82 (electrical signal conversion unit), a received-signal processing unit 83, a display control unit 85, the control unit 86, an input unit 87, the output unit 88, a storage unit 89, and the dust detecting unit 66. The control device 8 is connected to the camera head 6 via the transmission cable 7.

The connector 80 includes optical connection units 80a to 80d (receiver-side optical connection units). The optical cables 81a to 81d extend from the optical connection units 80a to 80d, respectively. The optical connection units 80a to 80d are provided to the distal ends serving as the input-side ends of the optical cables 81a to 81d, respectively. The optical connection units 80a to 80d are separably connected to the optical connection units 73a to 73d, respectively, in the connector 70 of the transmission cable 7 serving as an external member. The optical connection units 80a to 80d each include a GRIN lens connected to an optical fiber end surface of the optical cables 81a to 81d, respectively, and a cover glass that covers the surface of the GRIN lens. Connection surfaces of the optical connection unit 80a and the optical connection unit 73a of the transmission cable 7 come into contact with each other, thereby connecting the optical cable 71a and the optical cable 81a. Connection surfaces of the optical connection unit 80b and the optical connection unit 73b of the transmission cable 7 come into contact with each other, thereby connecting the optical cable 71b and the optical cable 81b. Connection surfaces of the optical connection unit 80c and the optical connection unit 73c of the transmission cable 7 come into contact with each other, thereby connecting the optical cable 71c and the optical cable 81c. Connection surfaces of the optical connection unit 80d and the optical connection unit 73d of the transmission cable 7 come into contact with each other, thereby connecting the optical cable 71d and the optical cable 81d.

The optical cables 81a to 81d transmit optical signals received by the optical connection units 80a to 80d, respectively, and output them to the O/E conversion unit 82.

The O/E conversion unit 82 converts the optical signals transmitted by the optical cables 81a to 81d into a plurality of serial electrical signals and outputs them to the received-signal processing unit 83.

The received-signal processing unit 83 converts the serial electrical signals converted by the O/E conversion unit 82 into parallel electrical signals. The received-signal processing unit 83 includes a clock data recovery (CDR) unit 83a, a K-code detecting unit 83b, a bit error rate (BER) detecting unit 83c, the transmission failure detection unit 83d, a decoding unit 83e, a first receiver-side signal conversion unit 831 (first serial conversion unit), a second receiver-side signal conversion unit 832 (second serial conversion unit), a switching unit 83j (second switching unit), and an image processing unit 83r. The received-signal processing unit 83, for example, is a programmable integrated circuit, such as an FPGA.

The CDR unit 83a performs CDR for reproducing superimposed clock signals from the received serial electrical signals. The CDR unit 83a outputs the execution result of CDR to the transmission failure detection unit 83d. If the CDR unit 83a receives all the serial electrical signals to be received and can perform CDR on all the serial electrical signals, the CDR unit 83a outputs the result to the transmission failure detection unit 83d. If the CDR unit 83a does not receive any one of the serial electrical signals to be received or may not perform CDR on all the serial electrical signals, the CDR unit 83a outputs, to the transmission failure detection unit 83d, the result that the CDR is not performed in association with information for identifying the optical cable that transmits the serial electrical signal on which the CDR fails to be performed.

The K-code detecting unit 83b performs K-code detection for detecting a K-code from the serial electrical signals from which the clock signals are reproduced and detecting a timing of data, thereby obtaining valid data. The K-code detecting unit 83b outputs the result of K-code detection to the transmission failure detection unit 83d. If the K-code detecting unit 83b can perform K-code detection on all the input signals, the K-code detecting unit 83b outputs the result to the transmission failure detection unit 83d. If the K-code detecting unit 83b may not perform K-code detection on all the input signals, the K-code detecting unit 83b outputs, to the transmission failure detection unit 83d, the result that the K-code detection is not performed in association with information for identifying the optical cable that transmits the serial electrical signal on which the K-code detection fails to be performed.

The BER detecting unit 83c performs BER detection for calculating the probability of receiving erroneous data out of the valid data of the serial electrical signals (digital data) detected by the K-code detecting unit 83b. The BER detecting unit 83c calculates a value by dividing the number of erroneous bits by the total number of received bits for each of the received serial electrical signals. The BER detecting unit 83c outputs the calculation result to the transmission failure detection unit 83d.

The transmission failure detection unit 83d detects transmission failure of the optical signals in the optical cables 71a to 71d. The transmission failure detection unit 83d identifies an optical cable having transmission failure out of the optical cables 71a to 71d. The transmission failure detection unit 83d detects transmission failure of the optical signals in the optical cables 71a to 71d based on the serial electrical signals converted by the O/E conversion unit 82. The transmission failure detection unit 83d determines whether transmission failure of the optical signals occurs in the optical cables 71a to 71d based on the result of CDR performed by the CDR unit 83a, the result of K-code detection performed by the K-code detecting unit 83b, or the result of BER detection performed by the BER detecting unit 83c. The CDR, the K-code detection, and the BER detection are performed on the serial electrical signals converted by the O/E conversion unit 82. The transmission failure detection unit 83d identifies the optical cable having the transmission failure.

The decoding unit 83e converts the serial electrical signals received from the BER detecting unit 83c into groups of parallel electrical signals. Subsequently, the decoding unit 83e performs Mb/Nb decoding on the parallel electrical signals of the respective groups resulting from the conversion. The decoding unit 83e outputs the parallel electrical signals to the first receiver-side signal conversion unit 831 and the second receiver-side signal conversion unit 832.

The first receiver-side signal conversion unit 831 includes a first serial (S) conversion unit 83f and a first shaping unit 83g. The first receiver-side signal conversion unit 831 converts the parallel electrical signals output from the decoding unit 83e, that is, the parallel electrical signals of the first group number equal to the number of the optical cables in the transmission cable 7 into a first serial electrical signal. In other words, the first receiver-side signal conversion unit 831 converts the parallel electrical signals of the first group number converted by the O/E conversion unit 82 into the same number of first serial electrical signals. In the example illustrated in FIG. 2, the optical cable group 71 in the transmission cable 7 includes the four optical cables 71a to 71d. The first S conversion unit 83f converts the parallel electrical signals of four groups output from the decoding unit 83e into four serial electrical signals. The first shaping unit 83g removes the delimiters supplied by the first distributing unit 64b from the four serial electrical signals converted by the first S conversion unit 83f. The first shaping unit 83g thus shapes the four serial electrical signals into the format of the original image signals, that is, the format of the image signals output from the image sensor 62 and outputs them as one first serial electrical signal.

The second receiver-side signal conversion unit 832 includes a second S conversion unit 83h and a second shaping unit 83i. The second receiver-side signal conversion unit 832 extends the parallel electrical signals output from the decoding unit 83e, that is, the parallel electrical signals of the second group number smaller than the first group number and converts them into a second serial electrical signal. In other words, the second receiver-side signal conversion unit 832 extends the parallel electrical signals of the second group number converted by the O/E conversion unit 82 and converts them into the same number of second serial electrical signals. In the example illustrated in FIG. 2, the decoding unit 83e outputs the parallel electrical signals of three groups the number of which is smaller than that of the optical cables 71a to 71d of the transmission cable 7 by 1. The second S conversion unit 83h extends the parallel electrical signals of three groups output from the decoding unit 83e and converts them into three serial electrical signals. The second shaping unit 83i removes the delimiters supplied by the second distributing unit 64d from the three serial electrical signals converted by the second S conversion unit 83h. The second shaping unit 83i thus shapes the three serial electrical signals into the format of the original image signals and outputs them as one second serial electrical signal. The second receiver-side signal conversion unit 832 performs division in a manner corresponding to the compression rate in the second transmitter-side signal conversion unit 642.

The switching unit 83j can switch the serial electrical signals to be received by the image processing unit 83r, which will be described later, between the first serial electrical signals and the second serial electrical signals under the control of the transmission failure detection unit 83d.

The switching unit 83*j* is a multiplexer, for example. The image signals received by the switching unit 83*j* may be received not as serial electrical signals but as parallel electrical signals. In this case, the first receiver-side signal conversion unit 831 and the second receiver-side signal conversion unit 832 output the image signals as parallel electrical signals without converting them into serial electrical signals.

The image processing unit 83*r* performs, under the control of the control unit 86, which will be described later, predetermined signal processing on the image signals output from the switching unit 83*j*, that is, the image signals in the RAW format or in the predetermined format with a low compression rate generated by the image sensor 62. The image processing unit 83*r* performs, on the image signals, various types of image processing including optical black subtraction, gain adjustment, synchronization of the image signals, gamma correction, white balance (WB) adjustment, a color matrix arithmetic operation, color reproduction, and edge enhancement.

The display control unit 85 generates display image signals used for display on the display device 9 from the image signals processed by the image processing unit 83*r*. The display image signals output to the display device 9 are digital signals in the format of serial digital interface (SDI), digital visual interface (DVI), or high-definition multimedia interface (HDMI) (registered trademark), for example. If the transmission failure detection unit 83*d* detects transmission failure in the optical cables 71*a* to 71*d* or the optical cable having the failure under the control of the control unit 86, the display control unit 85 generates alarm image signals indicating that transmission failure occurs in the optical cable. The display control unit 85 causes the display device 9 to output and display the alarm image. If the accumulation amount of dust detected by the dust detecting unit 66 under the control of the control unit 86 exceeds the predetermined threshold, the display control unit 85 generates alarm image signals indicating a potential risk of abnormal temperature rise in the apparatus. The display control unit 85 causes the display device 9 to output and display the alarm image.

The control unit 86 is embodied as a CPU, for example. The control unit 86 controls processing operations of each unit in the control device 8. The control unit 86, for example, transfers instruction information and data to each component of the control device 8, thereby controlling the operations of the control device 8. The control device 8 is connected to each component of the camera head 6 via each cable and controls the operations of the image sensor 62, the driving unit 63, and other components. The control unit 86 also controls the switching performed by the switching unit 64*e* of the camera head 6 and the switching unit 83*j* of the received-signal processing unit 83.

The control unit 86 changes the number and the destination of the serial electrical signals converted by the transmission signal processing unit 64 and output therefrom based on the result of detection performed by the transmission failure detection unit 83*d*. If the transmission failure detection unit 83*d* identifies an optical cable having transmission failure out of the optical cables 71*a* to 71*d*, the control unit 86 changes the number and the destination of the serial electrical signals converted by the transmission signal processing unit 64 such that a plurality of optical signals are distributed to the optical cables other than the optical cable having the transmission failure.

If the transmission failure detection unit 83*d* detects no transmission failure, all the four optical cables 71*a* to 71*d* can normally transmit the signals. In this case, the control unit 86 causes the switching unit 64*e* to select the electrical signals processed through a route R1 via the first transmitter-side signal conversion unit 641 as the output signals. In addition, the control unit 86 causes the switching unit 83*j* to select the electrical signals processed through a route R3 via the first receiver-side signal conversion unit 831 as the output signals. Selection of the electrical signals by the switching unit 64*e* and selection of the electrical signals by the switching unit 83*j* are set by default. Because the route R1 and the route R3 are selected in normal time, the routes R1 and R3 are hereinafter referred to as a normal route.

If the transmission failure detection unit 83*d* detects transmission failure in the four optical cables 71*a* to 71*d*, the control unit 86 causes the switching unit 64*e* to switch the output signals to the electrical signals processed through a route R2 via the second transmitter-side signal conversion unit 642. In addition, the control unit 86 causes the switching unit 83*j* to switch the output signals to the electrical signals processed through a route R4 via the second receiver-side signal conversion unit 832. The route R2 is a route to compress the received electrical signals and distribute them, whereas the route R4 is a route to extend the compressed electrical signals and aggregate them. The routes R2 and R4 are hereinafter referred to as a compression route.

The input unit 87 is embodied as an operating device, such as a mouse, a keyboard, and a touch panel, and receives input of various types of instruction information for the endoscope device 1. Specifically, the input unit 87 receives input of various types of instruction information, such as subject information (e.g., identification (ID), a birth date, and a name), identification information on the endoscope 2 (e.g., ID and examination items), and examination contents.

The output unit 88 is embodied as a speaker or a printer, for example, and outputs various types of information on internal observation. If the transmission failure detection unit 83*d* detects transmission failure in the optical cables 71*a* to 71*d* or the optical cable having the failure under the control of the control unit 86, the output unit 88 outputs an audio alarm indicating that transmission failure occurs in the optical cable. If the accumulation amount of dust detected by the dust detecting unit 66 under the control of the control unit 86 exceeds the predetermined threshold, the output unit 88 outputs an audio alarm indicating a potential risk of abnormal temperature rise in the apparatus.

The storage unit 89 is implemented with a volatile memory and a non-volatile memory and stores therein various programs to operate the camera head 6, the control device 8, and other devices. The storage unit 89 temporarily stores therein information that is being processed by the control device 8. The storage unit 89 stores therein an image signal picked up by the image sensor 62, and an image signal on which image processing is performed by the image processing unit 83*r*. The storage unit 89 may be implemented with a memory card and other medium attached from the outside of the control device 8.

Figure 5:
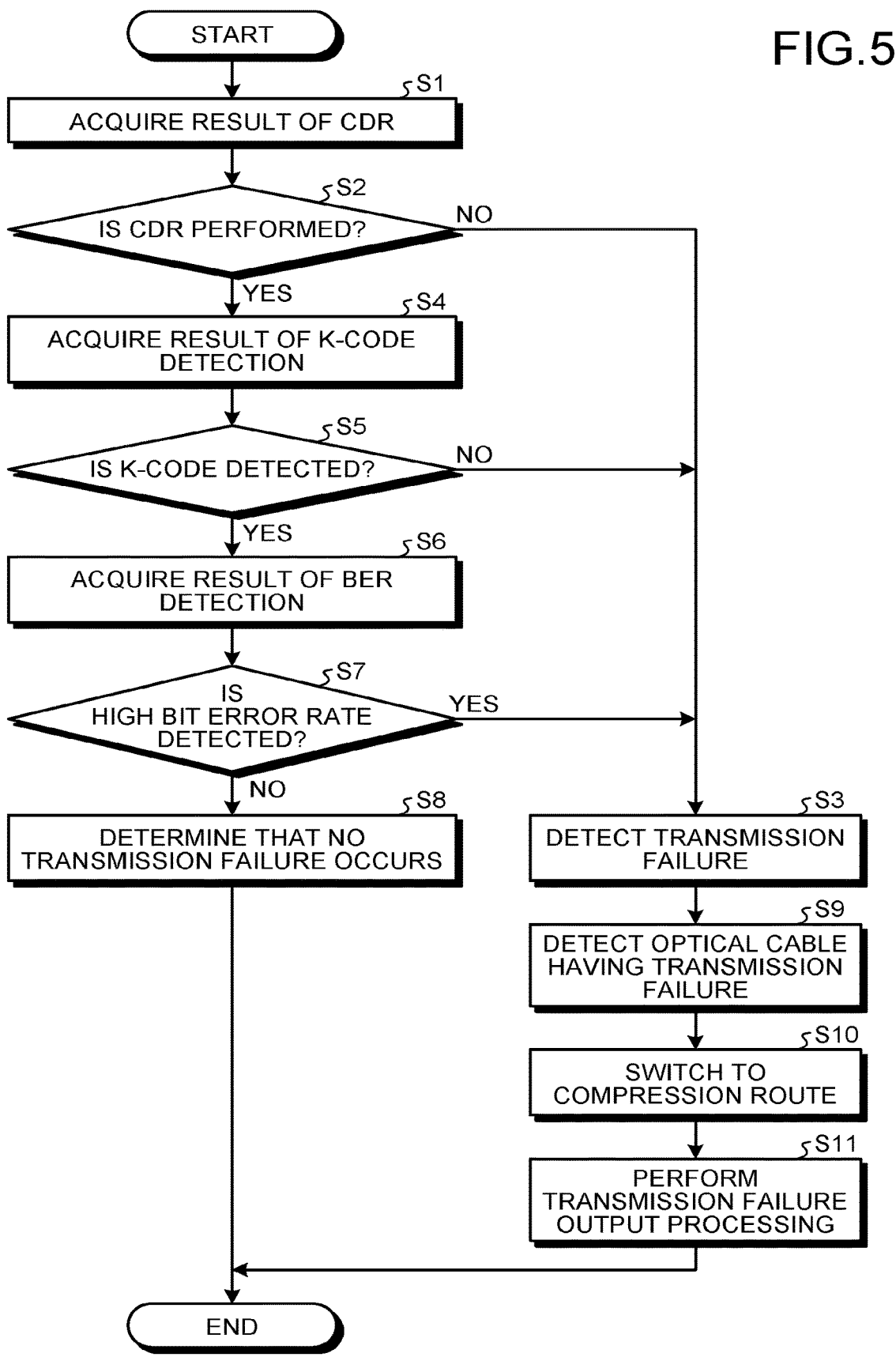
FIG. 5 is a flowchart of a procedure of transmission failure detection performed by the control device illustrated in FIG. 2.

Processing for transmission failure detection in the control device 8 illustrated in FIG. 2 will now be described. FIG. 5 is a flowchart of a processing procedure for transmission failure detection in the control device 8 illustrated in FIG. 2.

As illustrated in FIG. 5, the transmission failure detection unit 83*d* acquires the result of CDR performed on serial electrical signals received by the CDR unit 83*a* (Step S1). The transmission failure detection unit 83*d* determines whether the CDR is performed on all the serial electrical signals to be received by the CDR unit 83*a* (Step S2). When an optical fiber is broken, the optical cable including the broken optical fiber transmits no optical signal to the control device 8 serving as the receiver. As a result, no CDR is performed. If the transmission failure detection unit 83*d* determines that the CDR is not performed on all the serial electrical signals (No at Step S2), the transmission failure detection unit 83*d* detects that transmission failure occurs because of breakage or other causes in any one of the optical fibers in the optical cables (Step S3).

If the transmission failure detection unit 83*d* determines that the CDR is performed on all the serial electrical signals (Yes at Step S2), the transmission failure detection unit 83*d* acquires the result of K-code detection from the K-code detecting unit 83*b* (Step S4). Based on the acquired result of K-code detection, the transmission failure detection unit 83*d* determines whether the K-code is detected from all the input signals (Step S5). When an optical fiber is broken, the optical cable including the broken optical fiber transmits no optical signal to the control device 8 serving as the receiver. As a result, no K-code or no timing of data is detected. If the transmission failure detection unit 83*d* determines that the K-code is not detected from all the serial electrical signals (No at Step S5), the transmission failure detection unit 83*d* detects that transmission failure occurs because of breakage or other causes in any one of the optical fibers in the optical cables (Step S3).

If the transmission failure detection unit 83*d* determines that the K-code is detected from all the serial electrical signals (Yes at Step S5), the transmission failure detection unit 83*d* acquires the result of BER detection from the BER detecting unit 83*c* (Step S6). Based on the acquired result of BER detection, the transmission failure detection unit 83*d* determines whether a high bit error rate exceeding a predetermined threshold is detected from any one of the input signals (Step S7). When transmission failure or transmission degradation occurs in the optical cables, the optical intensity of the optical signals received by the O/E conversion unit 82 decreases, and the bit error rate in the BER detection increases. If the transmission failure detection unit 83*d* determines that no high bit error rate exceeding the predetermined threshold is detected from all the input signals (No at Step S7), the transmission failure detection unit 83*d* determines that no transmission failure occurs in all the optical cables (Step S8). Subsequently, the transmission failure detection is terminated.

By contrast, if the transmission failure detection unit 83*d* determines that a high bit error rate exceeding the predetermined threshold is detected from any one of the input signals (Yes at Step S7), the transmission failure detection unit 83*d* detects that transmission failure occurs because of breakage or other causes in any one of the optical fibers in the optical cables (Step S3). Subsequently, the transmission failure detection unit 83*d* detects an optical cable having the transmission failure out of the optical cables 71*a* to 71*d* (Step S9). At Step S9, the transmission failure detection unit 83*d* identifies, based on the result of CDR, the optical cable that transmits the serial electrical signal on which the CDR fails to be performed as the optical cable having the transmission failure. At Step S9, the transmission failure detection unit 83*d* identifies, based on the result of K-code detection, the optical cable that transmits the serial electrical signal on which the K-code detection fails to be performed as the optical cable having the transmission failure. If the transmission failure detection unit 83*d* acquires the result of BER detection including a high bit error rate from the BER detecting unit 83*c*, the transmission failure detection unit 83*d* identifies the optical cable that transmits the serial electrical signal indicating the high bit error rate as the optical cable having the transmission failure.

The control unit 86 performs switching from the normal route (routes R1 and R3) to the compression route (routes R2 and R4) such that the optical signals are distributed to the optical cables other than the optical cable determined to have the transmission failure by the transmission failure detection unit 83*d* (Step S10). Specifically, the transmission failure detection unit 83*d* causes the switching unit 64*e* to switch the output signals to the electrical signals processed through the route R2 via the second transmitter-side signal conversion unit 642. In addition, the control unit 86 causes the switching unit 83*j* to switch the output signals to the electrical signals processed through the route R4 via the second receiver-side signal conversion unit 832. As a result, the serial electrical signals compressed and divided into three by the second transmitter-side signal conversion unit 642 are transmitted to the O/E conversion unit 82 via the E/O conversion unit 65 and the three optical cables having no transmission failure. The three serial electrical signals are extended and converted by the second receiver-side signal conversion unit 832, and the electrical signals resulting from the extension and the conversion are received by the image processing unit 83*r*. Consequently, the image signals are continuously transmitted via the three optical cables having no transmission failure.

The control unit 86 performs transmission failure output processing for causing the display device 9 or the output unit 88 to output alarm information indicating that the transmission failure occurs (Step S11). The alarm information indicates not only the optical cable having the transmission failure but also the method for recovering from the transmission failure. Because the optical cable on which no CDR is performed or no K-code detection is performed highly possibly has a broken optical fiber, for example, the display device 9 or the output unit 88 outputs a message recommending maintenance, such as replacement of the optical cable, after an examination. Because the optical cable from which the high bit error rate is detected may possibly has dirt or tarnish on the optical connection unit of the connecter, the display device 9 or the output unit 88 outputs a message recommending cleaning of the optical connection unit after an examination. In this case, because the optical axis may possibly be misaligned at the optical connection unit, the display device 9 or the output unit 88 also outputs a message recommending correction of the optical axis.

The control device 8, for example, performs the processing from Step S1 to Step S11 during an examination performed by the endoscope device 1. The control device 8 may also perform the processing in an inspection before use and at the end of the examination.

As described above, if transmission failure occurs in any one of the optical cables during a procedure, the first embodiment uses the transmission path (routes R2 and R4) via the other three optical cables having no transmission failure. As a result, the optical signals (image signals) are continuously transmitted to the control device 8. In a case where an optical fiber in the optical cables is broken in the procedure, for example, the first embodiment can reliably prevent an image from suddenly disappearing during the procedure, thereby enabling the operator to appropriately continue the procedure. Also in a case where communication failure occurs because of dirt on the optical connection unit, misalignment of the optical axis, or aging deterioration, the first embodiment can prevent image noise caused by the transmission failure, thereby continuously displaying a clear image without noise. Because the first embodiment outputs the alarm information when detecting transmission failure at the optical connection unit, the first embodiment can prevent the transmission failure from being ignored.

Figure 6:
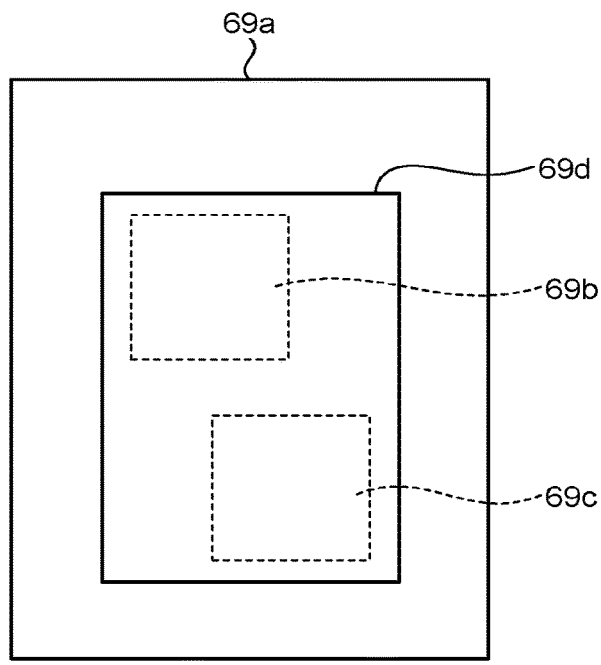
FIG. 6 is an example of a plan view of a major part in the control device illustrated in FIG. 2.
Figure 7:
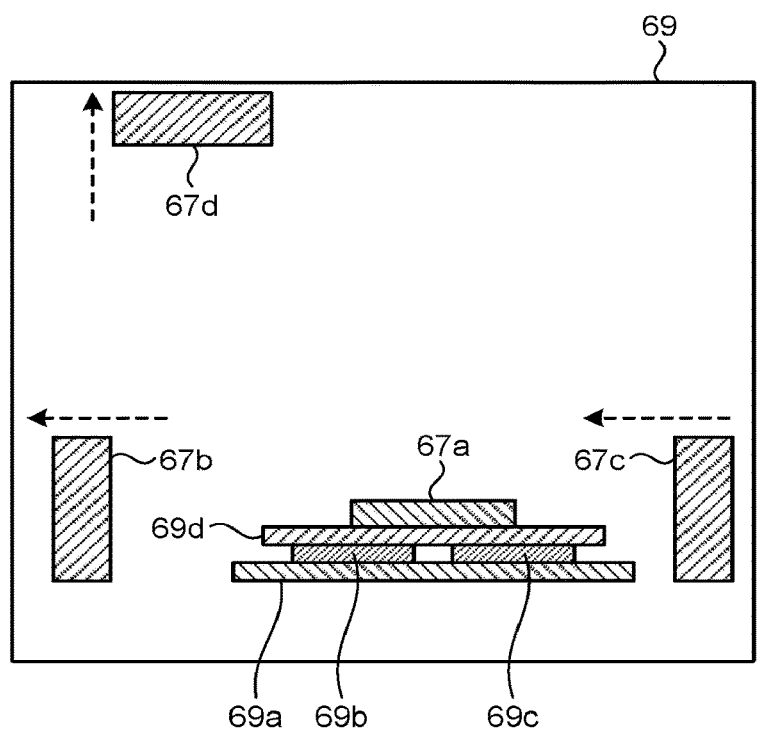
FIG. 7 is a sectional view obtained by cutting a case illustrated in FIG. 6 along a plane vertical to a substrate surface of a substrate.

FIG. 6 is an example of a plan view of a major part in the case of the control device 8. FIG. 7 is a sectional view obtained by cutting the case illustrated in FIG. 6 along a plane vertical to a substrate surface of a substrate in the case. As illustrated in FIGS. 6 and 7, a substrate 69a in the control device 8 is provided with devices that perform various types of processing, such as image capturing. Because the devices generally generate heat when driving, a fan or the like is usually provided to cool the heat generating devices. When fan lock occurs, however, the devices on the substrate may possibly fail because of the generated heat. In the first embodiment, a plurality of devices 69b and 69c that generate heat are connected with a member having high thermal conductivity, such as a heat sink 69d, with no dedicated fan for each chip. The heat sink 69d is cooled by a fan 67a on the heat sink 69d and a plurality of fans 67b to 67d in a case 69. With this configuration, the first embodiment avoids risk of a single failure in a cooling unit, such as fan lock. When a single failure, such as fan lock, occurs, the camera head 6 notifies the control device 8 of the failure and causes the display device 9 or the output unit 88 to output the alarm information.

First Modification of the First Embodiment

Figure 8:
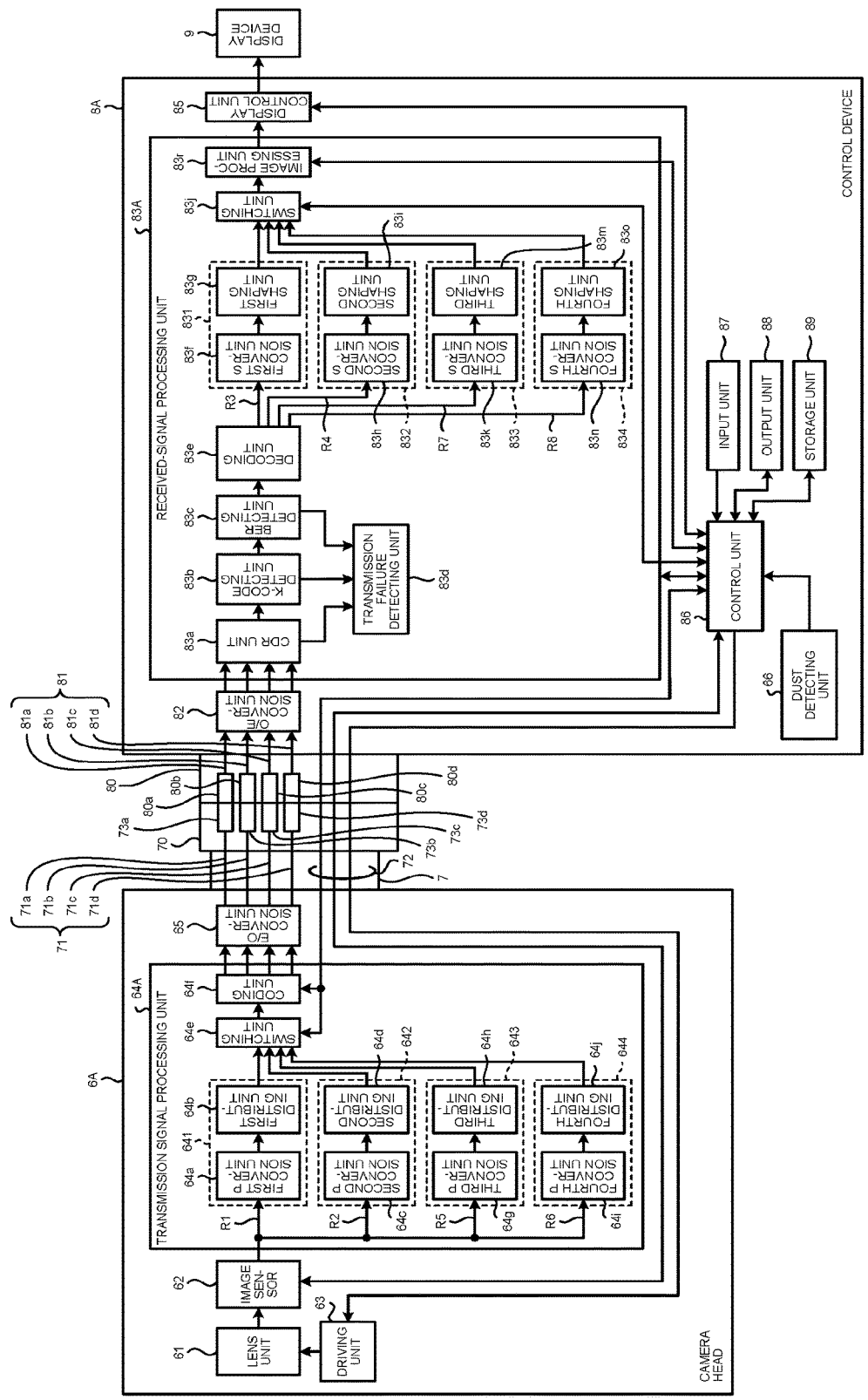
FIG. 8 is a block diagram of a configuration of a camera head in an endoscope, a transmission cable, and a control device according to a first modification of the first embodiment.

A first modification of the first embodiment describes an endoscope device that can address transmission failure occurring in two or more optical cables out of the four optical cables 71a to 71d constituting the optical cable group 71. FIG. 8 is a block diagram of a configuration of a camera head in an endoscope, a transmission cable, and a control device according to the first modification of the first embodiment.

As illustrated in FIG. 8, a camera head 6A according to the first modification of the first embodiment includes a third transmitter-side signal conversion unit 643 and a fourth transmitter-side signal conversion unit 644 besides the first transmitter-side signal conversion unit 641 and the second transmitter-side signal conversion unit 642 illustrated in FIG. 2 as a transmission signal processing unit 64A.

The third transmitter-side signal conversion unit 643 includes a third P conversion unit 64g and a third distributing unit 64h. The third P conversion unit 64g compresses the electrical signals output from the image sensor 62 to convert them into parallel signals of two groups. The third distributing unit 64h adjusts the parallel electrical signals of two groups converted by the third P conversion unit 64g in a manner enabling delimiters between the signals to be identified. The third distributing unit 64h distributes and outputs the parallel electrical signals in a manner corresponding to respective any two of the optical cables 71a to 71d. The fourth transmitter-side signal conversion unit 644 includes a fourth P conversion unit 64i and a fourth distributing unit 64j. The fourth P conversion unit 64i compresses the electrical signals output from the image sensor 62 to convert them into parallel signals of one group the number of which is smaller than that of the optical cables 71a to 71d by 3. The fourth distributing unit 64j adjusts the parallel signals of one group compressed by the fourth P conversion unit 64i in a manner enabling delimiters between the signals to be identified. The fourth distributing unit 64j outputs the parallel signals in a manner corresponding to any one of the optical cables 71a to 71d.

A control device 8A according to the first modification of the first embodiment includes a third receiver-side signal conversion unit 833 and a fourth receiver-side signal conversion unit 834 besides the first receiver-side signal conversion unit 831 and the second receiver-side signal conversion unit 832 illustrated in FIG. 2 as a received-signal processing unit 83A.

The third receiver-side signal conversion unit 833 includes a third S conversion unit 83k and a third shaping unit 83m. The third S conversion unit 83k extends the parallel electrical signals of two groups output from the decoding unit 83e to convert them into two serial electrical signals. The third shaping unit 83m removes the delimiters supplied by the third distributing unit 64h from the two serial electrical signals converted by the third S conversion unit 83k. The third shaping unit 83m thus shapes the two serial electrical signals into the format of the original image signals and outputs them as one third serial electrical signal. The fourth receiver-side signal conversion unit 834 includes a fourth S conversion unit 83n and a fourth shaping unit 83o. The fourth S conversion unit 83n extends the parallel electrical signals of one group output from the decoding unit 83e to convert them into the format of the original image signals, that is, one serial electrical signal. The fourth shaping unit 83o removes the delimiters supplied by the fourth distributing unit 64j from the serial electrical signal converted by the fourth S conversion unit 83n, thereby shaping the serial electrical signal into the format of the original image signals.

If the transmission failure detection unit 83d according to the first modification of the first embodiment detects transmission failure in one of the four optical cables 71a to 71d, the transmission failure detection unit 83d causes the switching unit 64e to switch the signals to be output to the coding unit 64f to the parallel electrical signals processed through the route R2 via the second transmitter-side signal conversion unit 642 similarly to the first embodiment. The transmission failure detection unit 83d also causes the switching unit 83j to switch the signals to be output to the image processing unit 83r to the serial electrical signals processed through the route R4 via the second receiver-side signal conversion unit 832.

If the transmission failure detection unit 83d detects transmission failure in two of the four optical cables 71a to 71d, the transmission failure detection unit 83d causes the switching unit 64e to switch the signals to be output to the coding unit 64f to the parallel electrical signals processed through a route R5 via the third transmitter-side signal conversion unit 643. The transmission failure detection unit 83d also causes the switching unit 83j to switch the signals to be output to the image processing unit 83r to the serial electrical signals processed through a route R7 via the third receiver-side signal conversion unit 833. If the transmission failure detection unit 83d detects transmission failure in three of the four optical cables 71a to 71d, the transmission failure detection unit 83d causes the switching unit 64e to switch the signals to be output to the coding unit 64f to the parallel electrical signals processed through a route R6 via the fourth transmitter-side signal conversion unit 644. The transmission failure detection unit 83d also causes the switching unit 83j to switch the signals to be output to the image processing unit 83r to the serial electrical signals processed through a route R8 via the fourth receiver-side signal conversion unit 834.

As described above, the first modification of the first embodiment includes the third transmitter-side signal conversion unit 643 and the third receiver-side signal conversion unit 833 that support optical transmission using two optical cables out of the four optical cables and the fourth transmitter-side signal conversion unit 644 and the fourth receiver-side signal conversion unit 834 that support optical transmission using one optical cable. This configuration can continuously transmit the optical signals when transmission failure occurs in two or more of the four optical cables 71a to 71d.

In a case where the transmission failure detection unit 83d detects transmission failure in one of the four optical cables 71a to 71d, the transmission failure detection unit 83d may perform control such that the signal processing and the transmission are carried out through the route R5 and the route R7 via the predetermined two optical cables without using all the other three optical cables.

Figure 9:
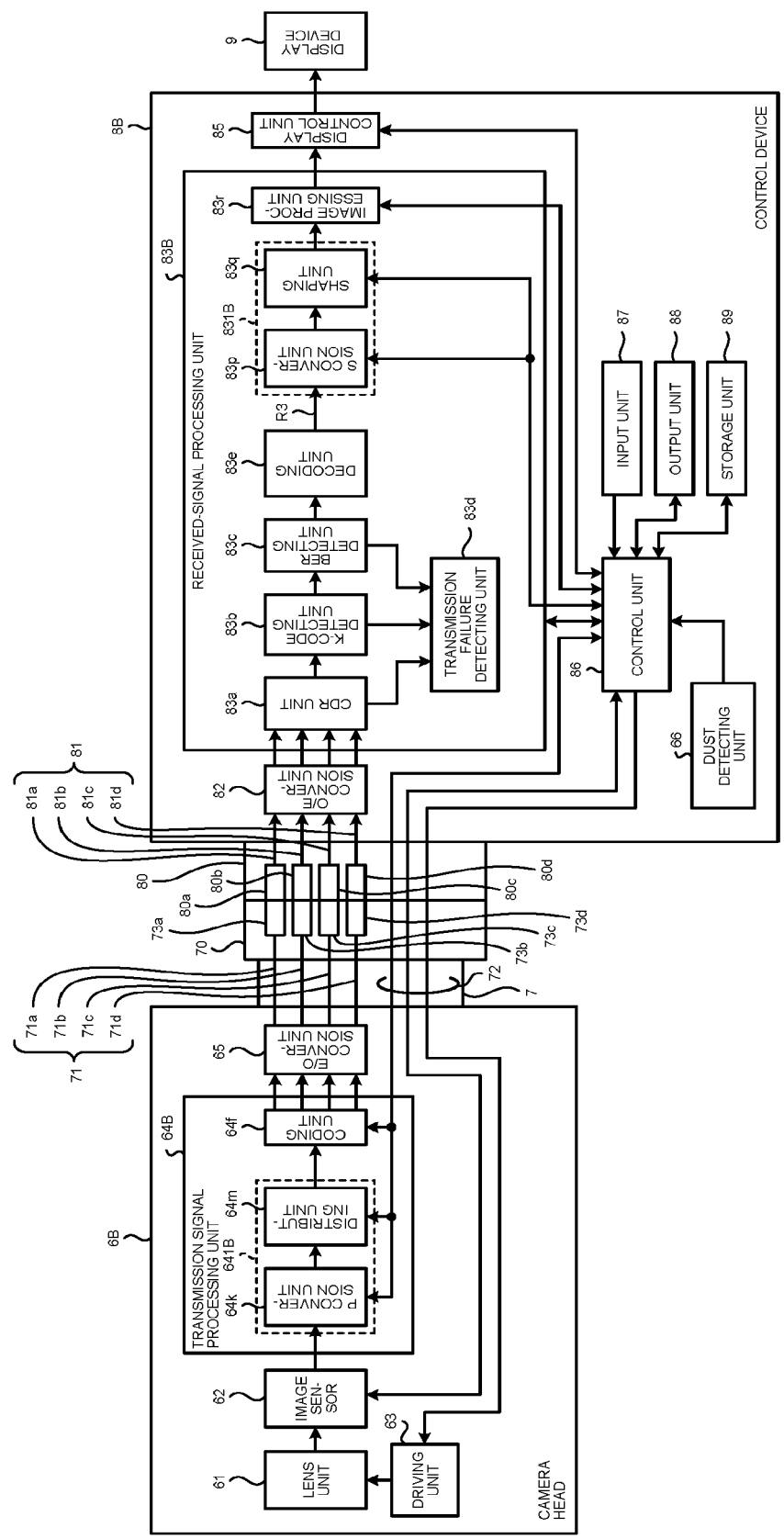
FIG. 9 is a block diagram of another configuration of the camera head in the endoscope, the transmission cable, and the control device according to the first modification of the first embodiment.

FIG. 9 is a block diagram of another configuration of the camera head in the endoscope, the transmission cable, and the control device according to the first modification of the first embodiment. In a camera head 6B illustrated in FIG. 9, a transmission signal processing unit 64B includes a transmitter-side signal conversion unit 641B instead of the first transmitter-side signal conversion unit 641 to the fourth transmitter-side signal conversion unit 644 and the switching unit 64e illustrated in FIG. 8.

The transmitter-side signal conversion unit 641B can change the compression rate for the electrical signals received from the image sensor 62, the number of groups of the parallel electrical signals resulting from conversion, and the distribution destinations of the parallel electrical signals of the respective groups. The transmitter-side signal conversion unit 641B includes a P conversion unit 64k and a distributing unit 64m. The P conversion unit 64k changes the compression rate for the electrical signals received from the image sensor 62 and the number of groups of the parallel electrical signals resulting from conversion under the control of the transmission failure detection unit 83d. The distributing unit 64m adjusts the parallel electrical signals of the respective groups converted by the P conversion unit 64k in predetermined units of bytes to shape them. Subsequently, the distributing unit 64m converts the parallel electrical signals of the respective groups into serial electrical signals and distributes them to optical cables the number of which corresponds to the conversion number in the P conversion unit 64k out of the optical cables 71a to 71d, that is, the optical cables specified by the control unit 86.

In a control device 8B illustrated in FIG. 9, a received-signal processing unit 83B includes a receiver-side signal conversion unit 831B instead of the first receiver-side signal conversion unit 831 to the fourth receiver-side signal conversion unit 834 and the switching unit 83j.

The receiver-side signal conversion unit 831B can change the extension rate for the parallel electrical signals output from the decoding unit 83e and the number of groups of the parallel signals to be converted into serial electrical signals. The receiver-side signal conversion unit 831B includes an S conversion unit 83p and a shaping unit 83q. The S conversion unit 83p extends the parallel electrical signals output from the decoding unit 83e in a manner corresponding to the conversion number and the distribution destinations of the serial electrical signals in the transmitter-side signal conversion unit 641B under the control of the transmission failure detection unit 83d. The S conversion unit 83p thus converts the parallel electrical signals into serial electrical signals. The shaping unit 83q removes the delimiters supplied by the distributing unit 64m from the serial electrical signals converted by the S conversion unit 83p. The shaping unit 83q thus shapes the serial electrical signals into the format of the original image and outputs them to the image processing unit 83r.

Based on the result of transmission failure detection performed by the transmission failure detection unit 83d, the control unit 86 changes the compression rate for the electrical signals, the number of groups in conversion into the parallel electrical signals, and the distribution destinations in the transmitter-side signal conversion unit 641B. The control unit 86 also changes the extension rate for the parallel electrical signals and the manner of shaping the parallel electric signals into the serial electrical signals in the receiver-side signal conversion unit 831B.

The first modification of the first embodiment may employ the configuration illustrated in FIG. 9. In the configuration, the control unit 86 can appropriately change the number of groups of the parallel electrical signals in conversion and the number of groups of the parallel signals to be converted into the serial electrical signals in accordance with the number of optical cables having transmission failure.

Second Modification of the First Embodiment

Figure 10:
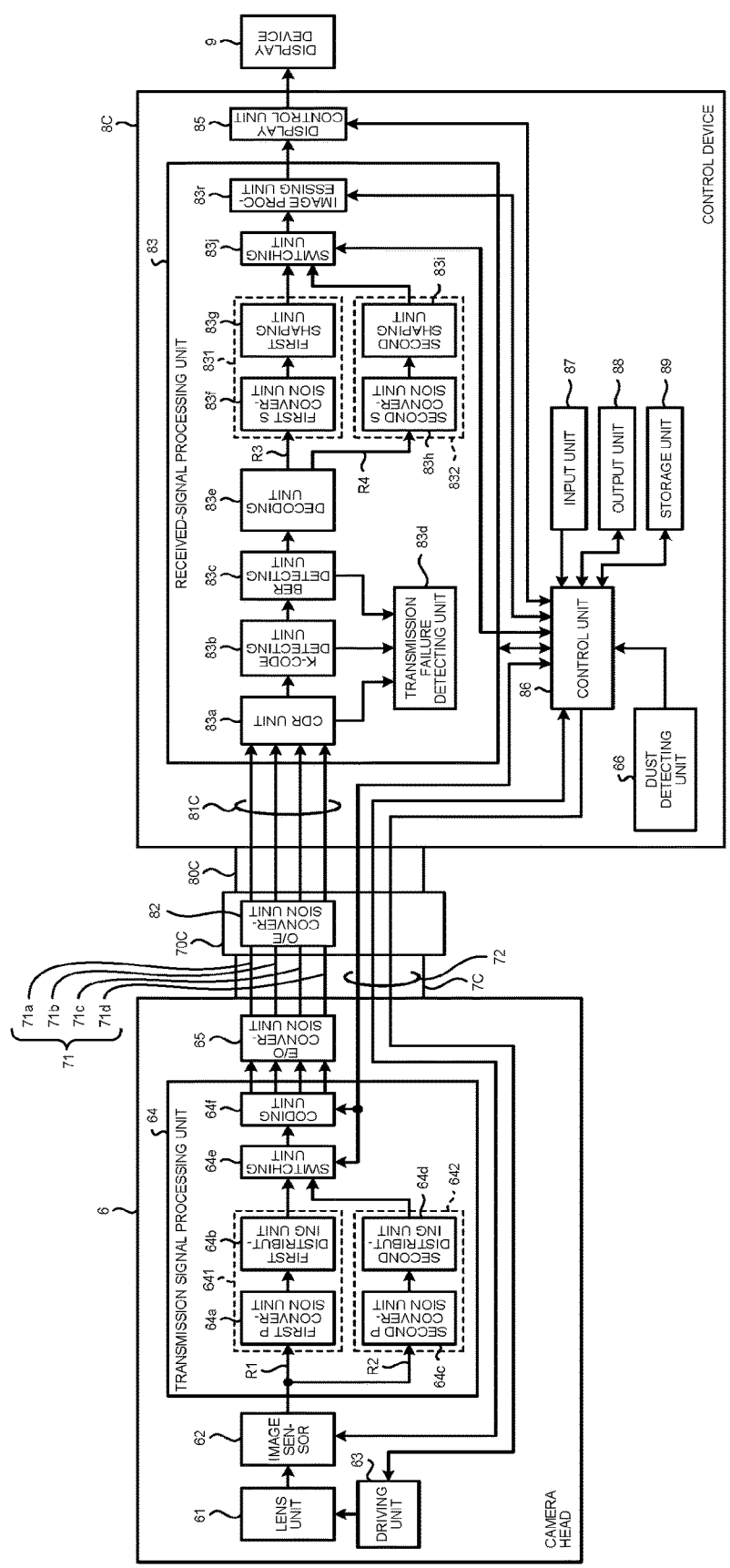
FIG. 10 is a block diagram of a configuration of a camera head in an endoscope, a transmission cable, and a control device according to a second modification of the first embodiment.

FIG. 10 is a block diagram of a configuration of a camera head in an endoscope, a transmission cable, and a control device according to a second modification of the first embodiment. As illustrated in FIG. 10, the O/E conversion unit 82 is removed from a control device 8C and is provided to a connector 70C of a transmission cable 7C compared with the configuration illustrated in FIG. 2. Optical signals transmitted via the optical cables 71a to 71d are converted into electrical signals by the O/E conversion unit 82 in the connector 70C. The electrical signals are then output to the received-signal processing unit 83 via four electrical wires 81C. With the configuration illustrated in FIG. 10, the connector 70C and a connector 80C of the control device 8C do not require the optical connection units 73a to 73d and 80a to 80d, respectively.

In a case where the O/E conversion unit 82 is provided to the connector 70C of the transmission cable 7C as illustrated in FIG. 10, signals can be transmitted from the transmission cable 7C to the control device 8C through the electrical wires. As a result, this configuration can suppress transmission failure and image noise caused by misalignment of the optical axis at the optical connection unit, dirt or tarnish on the connection surface of the optical connection unit, or other causes.

Second Embodiment

A second embodiment will now be described. In the second embodiment, the optical cable group includes a spare optical cable. When a transmission failure occurs in one of the normally used optical cables, optical signals are transmitted using the spare optical cable, instead of using the optical cable in which the transmission failure has occurred.

Figure 11:
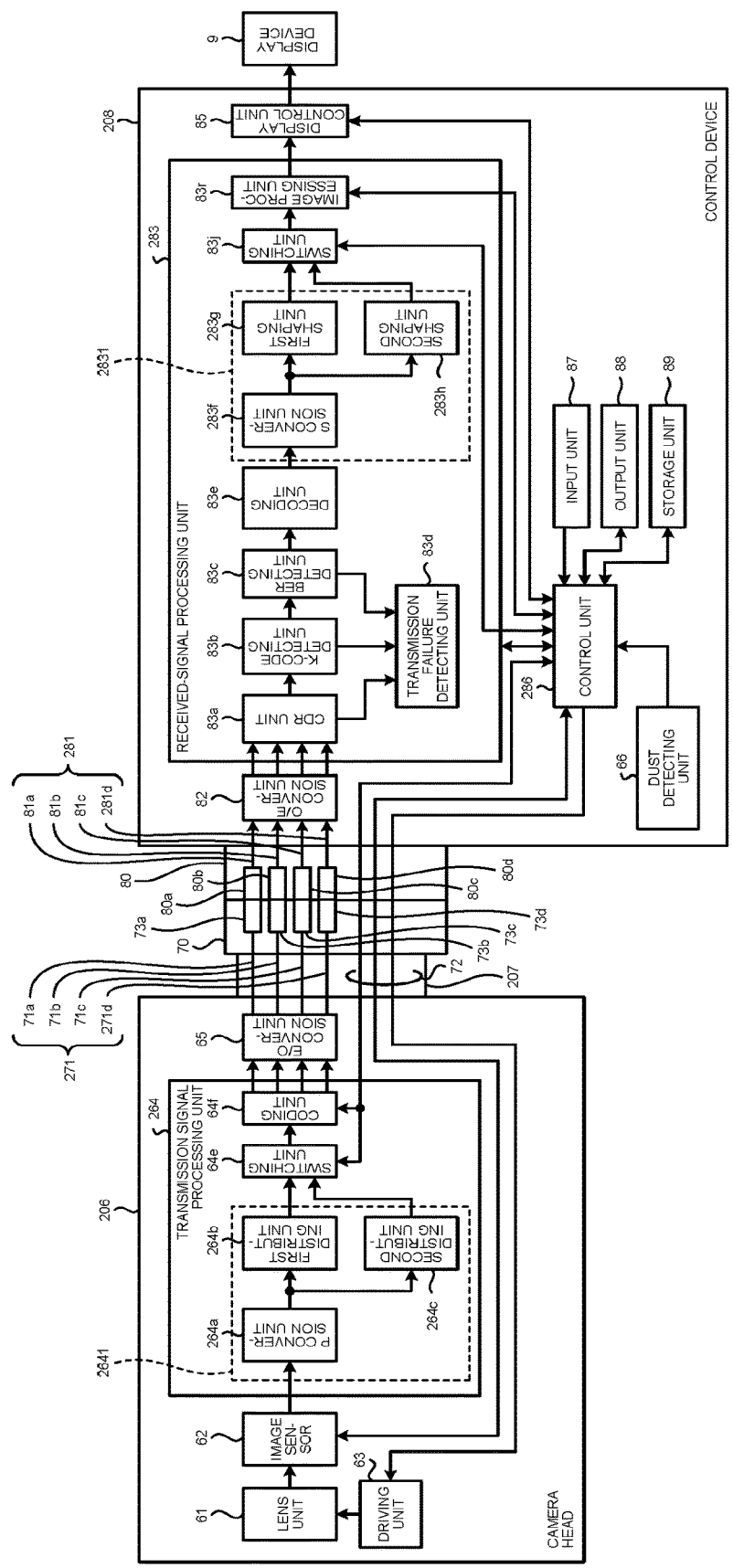
FIG. 11 is a block diagram of a configuration of a camera head in an endoscope, a transmission cable, and a control device according to a second embodiment of the present disclosure.

FIG. 11 is a block diagram of a configuration of a camera head, a transmission cable, and a control device of an endoscope according to a second embodiment. As illustrated in FIG. 11, a transmission cable 207 in the second embodiment includes a spare optical cable 271d in addition to the three normally used optical cables 71a to 71c as an optical cable group 271. The spare optical cable 271d can transmit at least one of the optical signals converted by the E/O conversion unit 65. In the transmission cable 207, the spare optical cable 271d is used to fill a gap between the other optical cables 71a to 71c, instead of a conventionally used support material. An optical cable group 281 at the side of a control device 208 includes a spare optical cable 281*d* in addition to the three normally used optical cables 81*a* to 81*c*.

A camera head 206 according to the second embodiment includes a transmission signal processing unit 264. The transmission signal processing unit 264 includes a transmitter-side signal conversion unit 2641 (parallel conversion unit) instead of the first transmitter-side signal conversion unit 641 and the second transmitter-side signal conversion unit 642 illustrated in FIG. 2.

The transmitter-side signal conversion unit 2641 includes a P conversion unit 264*a* (first conversion unit), a first distributing unit 264*b* (first distributing unit), and a second distributing unit 264*c* (second distributing unit). The transmitter-side signal conversion unit 2641 converts the electrical signals output from the image sensor 62 into parallel electrical signals of the first group number equal to the number of optical cables. In the example illustrated in FIG. 11, the transmitter-side signal conversion unit 2641 converts the electrical signals output from the image sensor 62 into parallel electrical signals of three groups the number of which is equal to that of the optical cables 71*a* to 71*c* normally used.

The P conversion unit 264*a* converts the electrical signals output from the image sensor 62 into parallel electrical signals of three groups. The first distributing unit 264*b* makes the parallel electrical signals of the respective groups converted by the P conversion unit 264*a* into a signal format for enabling them to be distributed to the respective optical cables 71*a* to 71*c*. The first distributing unit 264*b* adjusts the parallel electrical signals of three groups converted by the P conversion unit 264*a* in predetermined units of bytes. The first distributing unit 264*b* outputs the parallel electrical signals of the respective groups adjusted in a manner enabling delimiters between the signals to be identified so as to distribute the three parallel signals to the respective three optical cables 71*a* to 71*c*. The second distributing unit 264*c* makes the parallel electrical signals of the respective groups converted by the P conversion unit 264*a* into a signal format for enabling the signals to be distributed to optical cables other than an optical cable having transmission failure out of the optical cables 71*a* to 71*c* and to the spare optical cable 271*d*. The second distributing unit 264*c* adjusts the parallel electrical signals of the respective groups converted by the P conversion unit 264*a* in predetermined units of bytes. The second distributing unit 264*c* outputs the parallel electrical signals adjusted in a manner enabling delimiters between the signals to be identified so as to distribute the three parallel signals to the respective three optical cables including the spare optical cable 271*d*. The optical cable (e.g., the optical cable 71*a*) positioned outermost in the optical cable group 271 is generally susceptible to the effect of bending and other factors in the use of the transmission cable 207. As a result, the optical cable 71*a* is more likely to be broken than the other transmission cables 71*b* and 71*c* are, for example. To address this breaking, the second distributing unit 264*c* according to the second embodiment adjusts the parallel electrical signals, which have been divided into three groups by the conversion performed by the P conversion unit 264*a*, in a manner enabling delimiters between the signals to be identified so as to distribute the parallel electrical signals to the respective three optical cables 71*b*, 71*c*, and 271*d*. The second distributing unit 264*c* then outputs the adjusted parallel electrical signals. Subsequently, a plurality of serial electrical signals are output to the E/O conversion unit 65 via the switching unit 64*e* and the coding unit 64*f* similarly to the first embodiment.

The control device 208 according to the second embodiment includes a control unit 286 having the same functions as those of the control unit 86 illustrated in FIG. 2 and a received-signal processing unit 283. The received-signal processing unit 283 includes a receiver-side signal conversion unit 2831 (serial conversion unit) instead of the first receiver-side signal conversion unit 831 and the second receiver-side signal conversion unit 832 illustrated in FIG. 2.

The receiver-side signal conversion unit 2831 includes an S conversion unit 283*f* (second conversion unit), a first shaping unit 283*g* (first shaping unit), and a second shaping unit 283*h* (second shaping unit). The receiver-side signal conversion unit 2831 converts the parallel electrical signals of the first group number output from the decoding unit 83*e* into serial electrical signals. In the example illustrated in FIG. 11, the transmitter-side signal conversion unit 2641 converts the electrical signals output from the image sensor 62 into three serial electrical signals. The receiver-side signal conversion unit 2831 converts the parallel electrical signals of three groups output from the decoding unit 83*e* into three serial electrical signals.

The S conversion unit 283*f* converts the parallel electrical signals of three groups output from the decoding unit 83*e* into three serial electrical signals. The first shaping unit 283*g* shapes the serial electrical signals converted by the S conversion unit 283*f* from the signal format in the first distributing unit 264*b* to the signal format of the electrical signals output from the image sensor 62. The first shaping unit 283*g* removes the delimiters supplied by the first distributing unit 264*b* from the three serial electrical signals converted by the S conversion unit 283*f*. The first shaping unit 283*g* thus shapes the three serial electrical signals into the format of the original image signals, that is, the format of the image signals output from the image sensor 62 and outputs them. The second shaping unit 283*h* shapes the three serial electrical signals converted by the S conversion unit 283*f* from the signal format in the second distributing unit 264*c* to the signal format of the electrical signals output from the image sensor 62. The second shaping unit 283*h* removes the delimiters supplied by the second distributing unit 264*c* from the serial electrical signals converted by the S conversion unit 283*f*. The second shaping unit 283*h* thus shapes the serial electrical signals into the format of the original image signals, that is, the format of the image signals output from the image sensor 62 and outputs them.

If the transmission failure detection unit 83*d* detects transmission failure in the optical cable 71*a* out of the optical cables 71*a* to 71*c* normally used, the control unit 286 according to the second embodiment causes the transmitter-side signal conversion unit 2641 to distribute the optical signals to the optical cables 71*b*, 71*c*, and 271*d* including the spare optical cable 271*d*. In addition, the control unit 286 causes the receiver-side signal conversion unit 2831 to shape the serial electrical signals resulting from conversion in a manner corresponding to distribution of the serial electrical signals in the receiver-side signal conversion unit 2831.

If the transmission failure detection unit 83*d* detects no transmission failure in the three optical cables 71*a* to 71*c* normally used, the control unit 286 controls the switching unit 64*e* such that the parallel electrical signals output from the first distributing unit 264*b* are received by the coding unit 64*f*. In addition, the control unit 286 controls the switching unit 83*j* such that the serial electrical signals shaped by the first shaping unit 283*g* corresponding to the first distributing unit 264*b* are received by the image processing unit 83*r*. This switching control is set by default.

By contrast, if the transmission failure detection unit 83d detects transmission failure in the optical cable 71a, the control unit 286 performs control such that the serial electrical signals divided into three are transmitted through the optical cables 71b, 71c, and 271d. Specifically, the control unit 286 causes the switching unit 64e to switch the parallel electrical signals to be received by the coding unit 64f, that is, the parallel electrical signals corresponding to the serial electrical signals to be received by the E/O conversion unit 65, from the parallel electrical signals output from the first distributing unit 264b to the parallel electrical signals output from the second distributing unit 264c. In addition, the control unit 286 causes the switching unit 83j to switch the serial electrical signals to be received by the image processing unit 83r from the electrical signals shaped by the first shaping unit 283g to the electrical signals shaped by the second shaping unit 283h.

Figure 12:
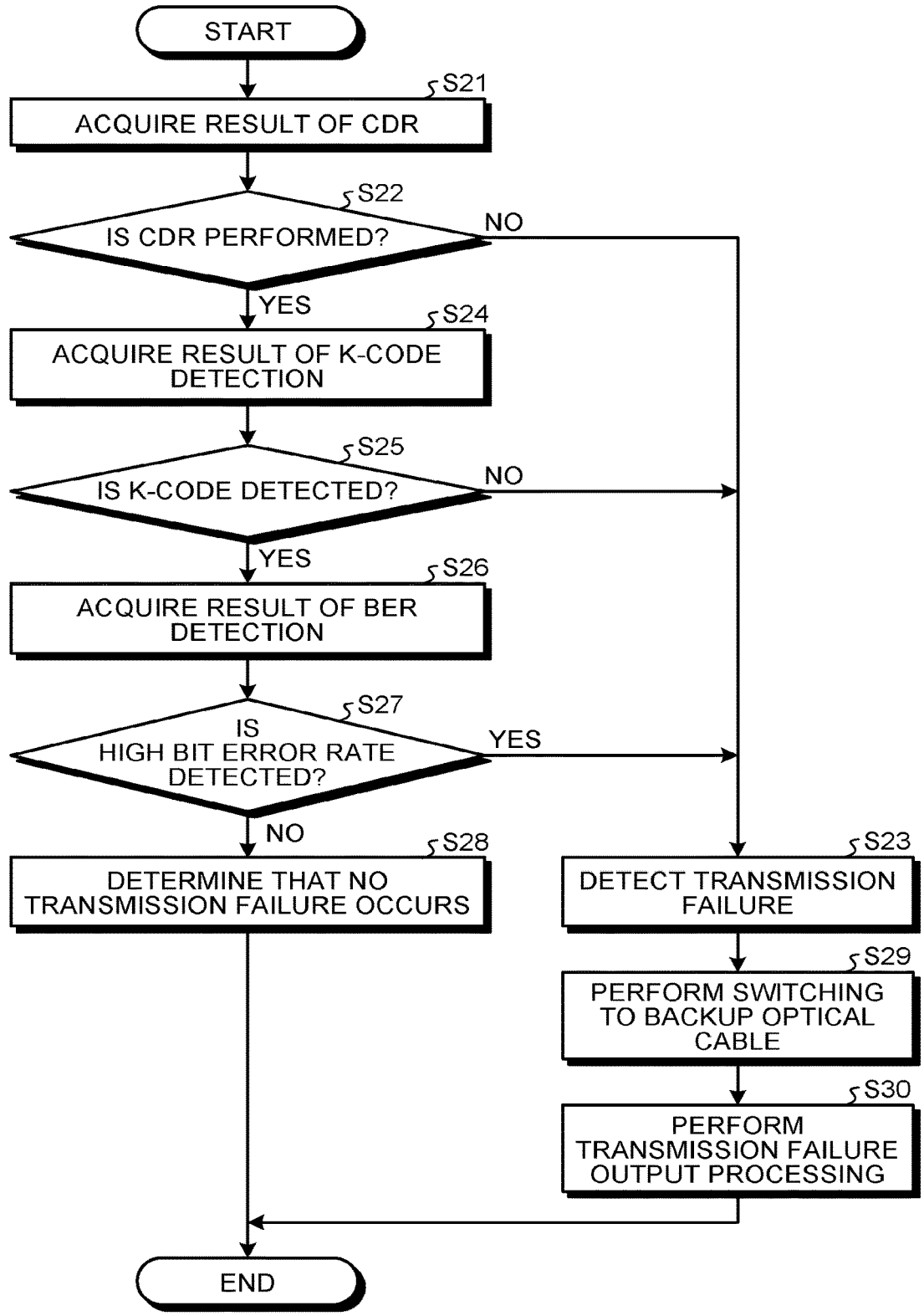
FIG. 12 is a flowchart of a procedure of transmission failure detection performed by the control device illustrated in FIG. 11.

FIG. 12 is a flowchart of a procedure of the transmission failure detection performed by the transmission failure detection unit illustrated in FIG. 11. The processing from Step S21 to Step S28 in FIG. 12 is the same as that from Step S1 to Step S8 in FIG. 5.

If the transmission failure detection unit 83d detects transmission failure at Step S23, the control unit 286 performs switching to the spare optical cable 271d such that the serial electrical signals divided into three groups are transmitted through the three optical cables 71b, 71c, and 271d including the spare optical cable 271d (Step S29). The control unit 286 causes the switching unit 64e to switch the parallel electrical signals to be received by the coding unit 64f from the parallel electrical signals output from the first distributing unit 264b to the parallel electrical signals output from the second distributing unit 264c. The control unit 286 also causes the switching unit 83j to switch the serial electrical signals to be received by the image processing unit 83r from the serial electrical signals shaped by the first shaping unit 283g to the serial electrical signals shaped by the second shaping unit 283h. The processing at Step S30 in FIG. 12 is the same as that at Step S11 in FIG. 5.

As described above, in a case where transmission failure occurs in any one of the three optical cables 71a to 71c during a procedure, the second embodiment uses the transmission path via the spare optical cable 271d having no transmission failure, thereby continuously transmitting the optical signals. Consequently, the second embodiment provides the same advantageous effects as those of the first embodiment.

The number of spare optical cables according to the second embodiment may be two or more. The physical number of optical cables simply needs to be more than that of optical fibers actually used in transmission.

First Modification of the Second Embodiment

Figure 13:
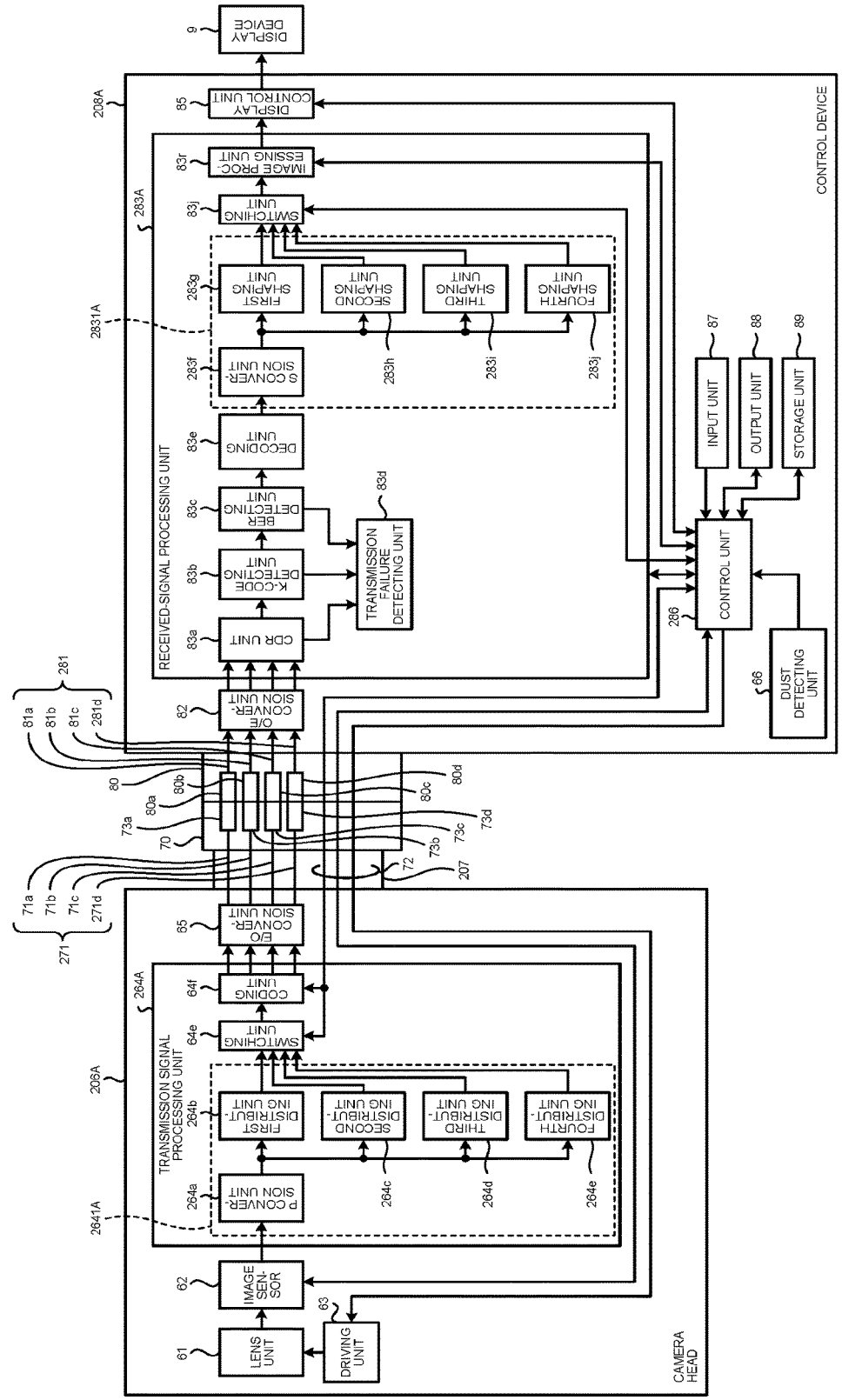
FIG. 13 is a block diagram of a configuration of a camera head in an endoscope, a transmission cable, and a control device according to a first modification of the second embodiment.

A first modification of the second embodiment describes an endoscope device that can address transmission failure occurring in any one of the three optical cables 71a to 71c normally used. FIG. 13 is a block diagram of a configuration of a camera head in an endoscope, a transmission cable, and a control device according to the first modification of the second embodiment.

As illustrated in FIG. 13, in a camera head 206A according to the first modification of the second embodiment, a transmission signal processing unit 264A includes a transmitter-side signal conversion unit 2641A. The transmitter-side signal conversion unit 2641A further includes a third distributing unit 264d and a fourth distributing unit 264e compared with the transmitter-side signal conversion unit 2641 illustrated in FIG. 11. If transmission failure occurs in the optical cable 71b, the third distributing unit 264d adjusts the parallel electrical signals of three groups converted by the P conversion unit 264a in predetermined units of bytes. The third distributing unit 264d outputs serial electrical signals adjusted in a manner enabling delimiters between the signals to be identified so as to distribute the three serial signals to the three optical cables 71a, 71c, and 271d. If transmission failure occurs in the optical cable 71c, the fourth distributing unit 264e adjusts the parallel electrical signals of three groups converted by the P conversion unit 264a in predetermined units of bytes. The fourth distributing unit 264e outputs serial electrical signals adjusted in a manner enabling delimiters between the signals to be identified so as to distribute the three serial signals to the three optical cables 71a, 71b, and 271d.

In a control device 208A according to the first modification of the second embodiment, a received-signal processing unit 283A further includes a third shaping unit 283i and a fourth shaping unit 283j compared with the configuration illustrated in FIG. 11. The third shaping unit 283i shapes the signals from the signal format in the third distributing unit 264d to the signal format of the electrical signals output from the image sensor 62. The fourth shaping unit 283j shapes the signals from the signal format in the fourth distributing unit 264e to the signal format of the electrical signals output from the image sensor 62. The third shaping unit 283i removes the delimiters supplied by the third distributing unit 264d from the serial electrical signals converted by the S conversion unit 283f. The third shaping unit 283i thus shapes the serial electrical signals into the format of the original image signals, that is, the format of the image signals output from the image sensor 62 and outputs them. The fourth shaping unit 283j removes the delimiters supplied by the fourth distributing unit 264e from the serial electrical signals converted by the S conversion unit 283f. The fourth shaping unit 283j thus shapes the serial electrical signals into the format of the original image signals and outputs them.

If transmission failure is detected in any one of the optical cables 71a to 71c normally used, the control unit 286 causes the transmitter-side signal conversion unit 2641A to distribute the optical signals to the spare optical cable 271d instead of the optical cable having the transmission failure. In addition, the control unit 286 causes a receiver-side signal conversion unit 2831A to shape the received electrical signals in a manner corresponding to distribution of the optical signals in the transmitter-side signal conversion unit 2641A.

Figure 14:
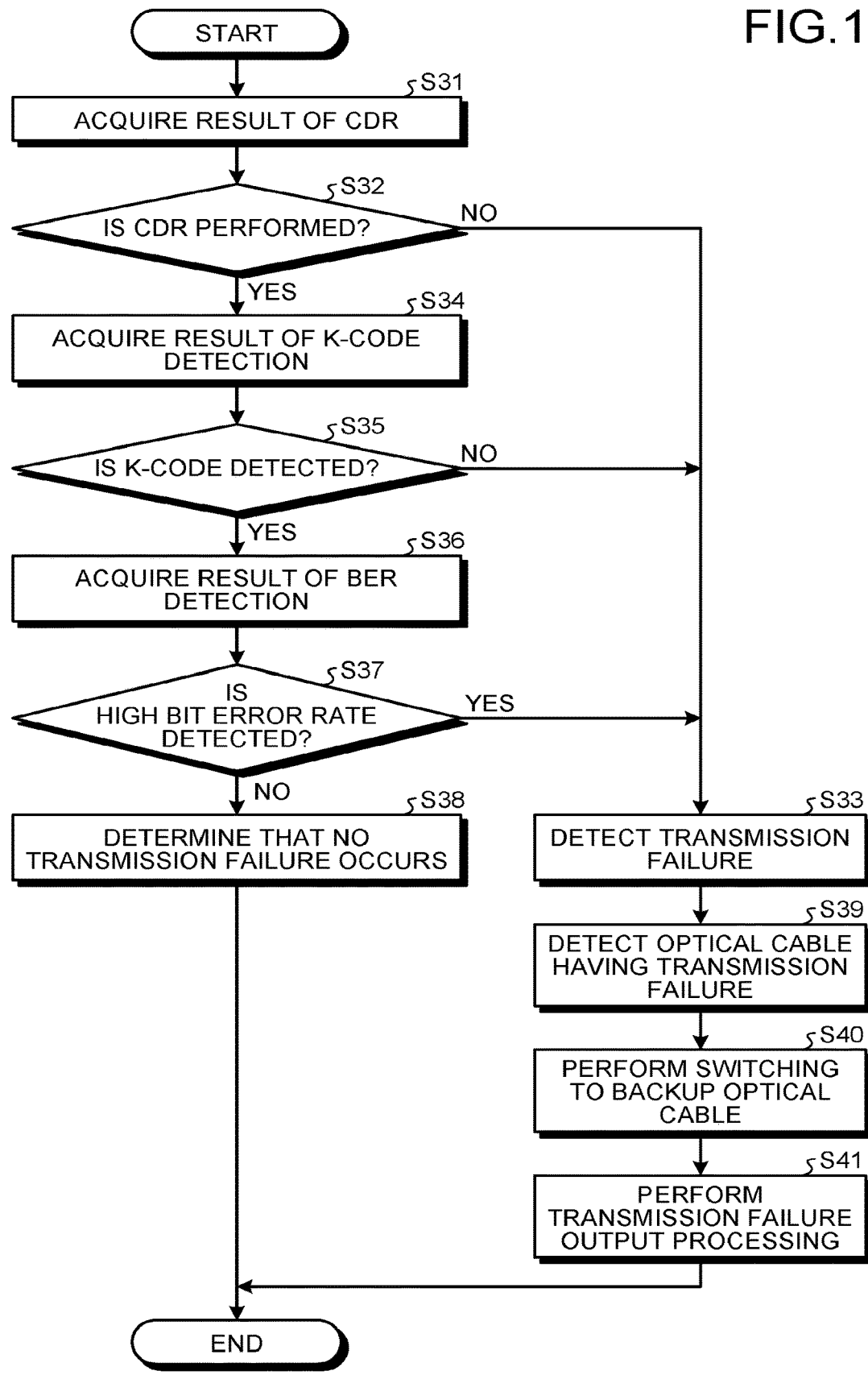
FIG. 14 is a flowchart of a procedure of transmission failure detection performed by the control device illustrated in FIG. 13.

FIG. 14 is a flowchart of a procedure of the transmission failure detection performed by the transmission failure detection unit illustrated in FIG. 13. The processing from Step S31 to Step S38 in FIG. 14 is the same as that from Step S21 to Step S28 in FIG. 12. The processing at Step S39 in FIG. 14 is the same as that at Step S9 in FIG. 5.

After the transmission failure detection unit 83d detects an optical cable having transmission failure at Step S39, the transmission failure detection unit 83d performs switching to the spare optical cable 271d such that the serial electrical signals divided into three are transmitted through the three optical cables including the spare optical cable 271d (Step S40).

Specifically, if the transmission failure detection unit 83d detects transmission failure in the optical cable 71a, the control unit 286 causes the switching unit 64e to switch the parallel optical signals to be received by the coding unit 64f to the parallel electrical signals output from the second distributing unit 264c. In addition, the control unit 286 causes the switching unit 83j to switch the serial electrical signals to be received by the image processing unit 83r to the serial electrical signals shaped by the second shaping unit 283h. If the transmission failure detection unit 83d detects transmission failure in the optical cable 71b, the control unit 286 causes the switching unit 64e to switch the parallel electrical signals to be received by the coding unit 64f to the parallel electrical signals output from the third distributing unit 264d. In addition, the control unit 286 causes the switching unit 83j to switch the serial electrical signals to be received by the image processing unit 83r to the serial electrical signals shaped by the third shaping unit 283i. If the transmission failure detection unit 83d detects transmission failure in the optical cable 71c, the control unit 286 causes the switching unit 64e to switch the parallel optical signals to be received by the coding unit 64f to the parallel electrical signals output from the fourth distributing unit 264e. In addition, the control unit 286 causes the switching unit 83j to switch the serial electrical signals to be received by the image processing unit 83r to the serial electrical signals shaped by the fourth shaping unit 283j. The processing at Step S41 in FIG. 14 is the same as that at Step S30 in FIG. 12.

As described above, the first modification of the second embodiment includes the third distributing unit 264d and the fourth distributing unit 264e in the transmitter-side signal conversion unit 2641A and the third shaping unit 283i and the fourth shaping unit 283j in the receiver-side signal conversion unit 2831A in a manner corresponding thereto. This configuration can address transmission failure occurring in any one of the three optical cables 71a to 71c normally used. Consequently, the first modification of the second embodiment can continuously transmit the optical signals more reliably.

Second Modification of the Second Embodiment

Figure 15:
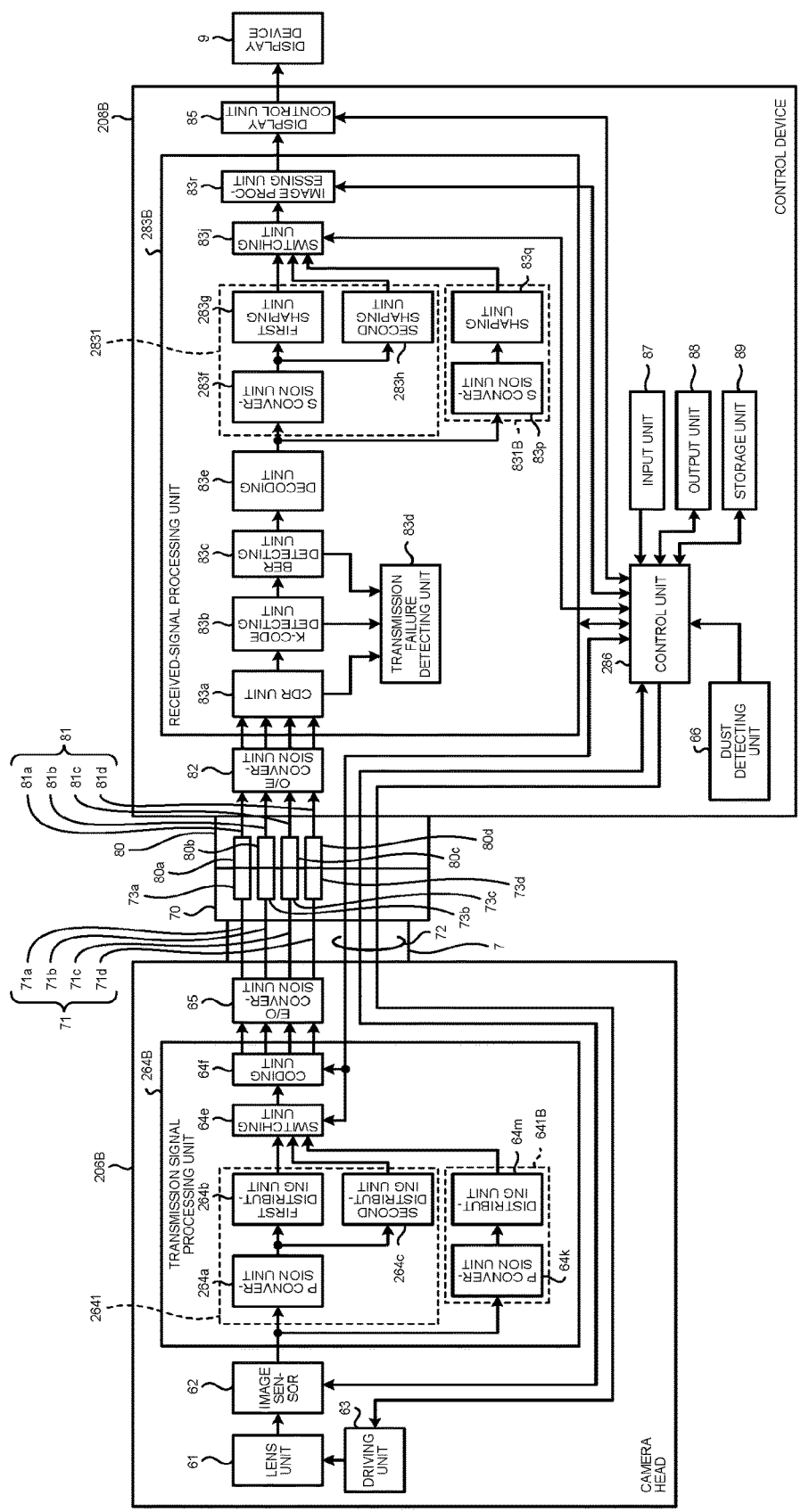
FIG. 15 is a block diagram of a configuration of a camera head in an endoscope, a transmission cable, and a control device according to a second modification of the second embodiment.

A second modification of the second embodiment describes an endoscope device that can address transmission failure occurring in optical cables the number of which is larger than that of spare optical cables. FIG. 15 is a block diagram of a configuration of a camera head in an endoscope, a transmission cable, and a control device according to the second modification of the second embodiment.

As illustrated in FIG. 15, in a camera head 206B according to the second modification of the second embodiment, a transmission signal processing unit 264B further includes the transmitter-side signal conversion unit 641B illustrated in FIG. 9 compared with the transmission signal processing unit 264 illustrated in FIG. 11. In a control device 208B according to the second modification of the second embodiment, a received-signal processing unit 283B further includes the receiver-side signal conversion unit 831B illustrated in FIG. 9 compared with the received-signal processing unit 283 illustrated in FIG. 11.

If transmission failure occurs in the optical cable 71a out of the optical cables 71a to 71c normally used, the control unit 286 performs control similarly to that in the second embodiment. Specifically, the control unit 286 causes the switching unit 64e to switch the parallel optical signals to be received by the coding unit 64f to the parallel electrical signals output from the second distributing unit 264c. In addition, the control unit 286 causes the switching unit 83j to switch the serial electrical signals to be received by the image processing unit 83r to the serial electrical signals shaped by the second shaping unit 283h.

If transmission failure occurs in two of the optical cables 71a to 71c normally used, for example, the control unit 286 controls the transmitter-side signal conversion unit 641B and the receiver-side signal conversion unit 831B so as to transmit the optical signals using two optical cables of the spare optical cable 271d and the normal optical cable out of the optical cables 71a to 71c.

Specifically, the control unit 286 changes the compression rate for the electrical signals in the P conversion unit 64k (third conversion unit) such that two parallel electrical signals output from the transmitter-side signal conversion unit 641B are distributed to the two optical cables of the normal optical cable and the spare optical cable 271d. The control unit 286 controls the distribution destinations from the distributing unit 64m (third distributing unit). The control unit 286 causes the switching unit 64e to switch the parallel optical signals to be received by the coding unit 64f to the parallel electrical signals output from the distributing unit 64m. The control unit 286 causes the receiver-side signal conversion unit 831B to change the following factors: the extension rate for the parallel electrical signals in the S conversion unit 83p (fourth conversion unit), the number of parallel electrical signals to be converted into serial electrical signals, and the contents of shaping of the serial electrical signals resulting from conversion in the shaping unit 83q (third shaping unit). These factors are changed in a manner corresponding to the number of groups in conversion and the distribution destinations of the parallel electrical signals in the transmitter-side signal conversion unit 641B. The control unit 286 causes the switching unit 83j to switch the serial electrical signals to be received by the image processing unit 83r to the serial electrical signals shaped by the shaping unit 83q.

As described above, the second embodiment may be combined with the first embodiment, making it possible to appropriately changing the number of parallel electrical signals in conversion and the number of parallel signals to be converted into serial electrical signals in accordance with the number of optical cables having transmission failure. This configuration can continuously transmit the optical signals more reliably.

Third Modification of the Second Embodiment

Figure 16:
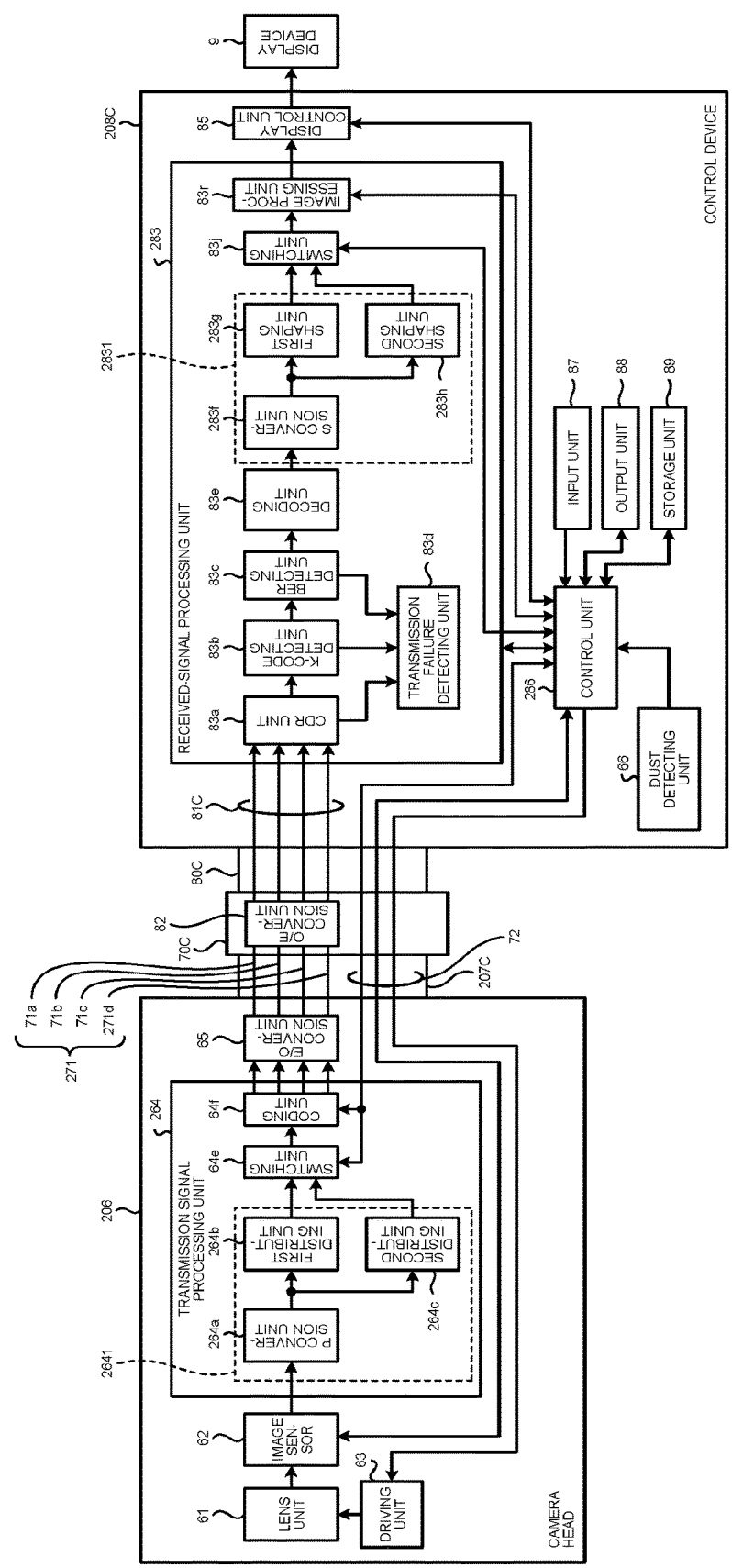
FIG. 16 is a block diagram of a configuration of a camera head in an endoscope, a transmission cable, and a control device according to a third modification of the second embodiment.

FIG. 16 is a block diagram of a configuration of a camera head in an endoscope, a transmission cable, and a control device according to a third modification of the second embodiment. As illustrated in FIG. 16, the third modification of the second embodiment has the configuration similar to that of the second modification of the first embodiment. Specifically, the O/E conversion unit 82 is removed from a control device 208C and is provided to the connector 70C of a transmission cable 207C. As a result, the optical connection units 73a to 73d and 80a to 80d are removed from the connector 70C and the connector 80C of the control device 208C, respectively. Also in this case, signals can be transmitted from the transmission cable 207C to the control device 208C through the electrical wires similarly to the second modification of the first embodiment. As a result, this configuration can prevent transmission failure and image noise caused by misalignment of the optical axis at the optical connection unit, dirt or tarnish on the connection surface of the optical connection unit, or other causes.

The first and the second embodiments are applicable not only to endoscope devices but also to medical observation apparatuses, such as operating microscopes, that capture an enlarged image of a minute site in a subject to generate image data of video. The first and the second embodiments may be applied not only to endoscope devices in the medical field but also to endoscope devices in the industrial field that observe the inside of an observation target, such as a mechanical structure.

The execution program for the processing performed by the control devices 8, 8A, 8B, 8C, 208, 208A, 208B, 208C, and other components according to the embodiments above may be recorded and provided in a computer-readable recording medium, such as a compact disc read only memory (CD-ROM), a flexible disk (FD), a compact disc recordable (CD-R), and a digital versatile disc (DVD), as an installable or executable file. The execution program may be stored in a computer connected to a network, such as the Internet, and provided by being downloaded via the network. Furthermore, the execution program may be provided or distributed via a network, such as the Internet.

The medical observation apparatus according to the present disclosure includes a transmission failure detection unit. The medical observation apparatus can detect transmission failure of optical signals in a plurality of optical transmission paths. Furthermore, the medical observation apparatus changes the number of parallel electrical signals resulting from conversion performed by a serial/parallel conversion unit and the number of parallel electrical signals to be converted into serial electrical signals by a parallel/serial conversion unit so as to transmit the optical signals without using an optical transmission path having the transmission failure. With this configuration, the medical observation apparatus can continuously transmit image signals to a control device.

It should be understood by those skilled in the art that various modifications, combinations, sub-combinations and alterations may occur depending on design requirements and other factors insofar as they are within the scope of the appended claims or the equivalents thereof.

What is claimed is:

1. A medical observation apparatus comprising:
   a first cable configured to transmit signals;
   a second cable configured to transmit signals;
   a processor configured to connect to the first cable and the second cable and generate a display image from the signals transmitted on the first cable and the signals transmitted on the second cable;
   an imaging device configured to connect to the first cable and the second cable and having an imager; and
   a transmission failure detection circuit configured to detect transmission failure of the second cable;
   wherein the imaging device configured to convert an imaging signal generated by the imager into a first signal and a second signal which are parallel and input the first signal and the second signal to the first cable and the second cable when the second cable is normal, and configured to generate a third signal generated by compressing the imaging signal and input the third signal to the first cable when the second cable is abnormal, and
   wherein both of the first cable and the second cable are optical fibers.

2. The medical observation apparatus according to claim 1, wherein the imaging device configured to not input the third signal to the second cable when the second cable is abnormal.

\* \* \* \* \*